US012564687B2

(12) United States Patent
Atterbury et al.

(10) Patent No.: US 12,564,687 B2
(45) Date of Patent: Mar. 3, 2026

(54) DEVICES AND PROCESSES FOR DELIVERY OF THERAPEUTIC FLUIDS

(71) Applicant: Eli Lilly and Company, Indianapolis, IN (US)

(72) Inventors: William Godwin Atterbury, Columbus, OH (US); Corrie Jo Bennison, Lewis Center, OH (US); Yelena N. Davis, Worthington, OH (US); Jeffrey Leclair Ellis, Columbus, OH (US); David Arthur Holley, Lancaster, OH (US); John Paul Tallarico, Powell, OH (US); Jessica Diane Young, Columbus, OH (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 547 days.

(21) Appl. No.: 18/044,657

(22) PCT Filed: Sep. 1, 2021

(86) PCT No.: PCT/US2021/048576
§ 371 (c)(1),
(2) Date: Mar. 9, 2023

(87) PCT Pub. No.: WO2022/055760
PCT Pub. Date: Mar. 17, 2022

(65) Prior Publication Data
US 2023/0364353 A1 Nov. 16, 2023

Related U.S. Application Data

(60) Provisional application No. 63/077,018, filed on Sep. 11, 2020.

(51) Int. Cl.
| | | |
|---|---|---|
| A61M 5/32 | (2006.01) | |
| A61M 5/20 | (2006.01) | |
| A61M 39/26 | (2006.01) | |

(52) U.S. Cl.
CPC ........ *A61M 5/3234* (2013.01); *A61M 5/2053* (2013.01); *A61M 39/26* (2013.01); *A61M 2205/36* (2013.01); *A61M 2205/50* (2013.01)

(58) Field of Classification Search
CPC .. A61M 5/3234; A61M 5/2053; A61M 39/26; A61M 2205/36; A61M 2205/50
(Continued)

(56) References Cited

U.S. PATENT DOCUMENTS

| | | | | |
|---|---|---|---|---|
| 2014/0323982 A1* | 10/2014 | Lumme | ............... | A61M 5/3234 604/218 |
| 2014/0330216 A1* | 11/2014 | Weaver | ............... | A61M 5/3232 29/469 |
| 2019/0307959 A1 | 10/2019 | Guillermo | | |

FOREIGN PATENT DOCUMENTS

| | | |
|---|---|---|
| EP | 2596823 | 5/2013 |
| WO | 2013/119591 | 8/2013 |

(Continued)

OTHER PUBLICATIONS

International Search Report of the International Searching Authority pertaining to International Application No. PCT/US2021/048576; Date of Mailing: Dec. 14, 2021; 5 pages.
(Continued)

*Primary Examiner* — Phillip A Gray
(74) *Attorney, Agent, or Firm* — Jonathan C. Anderson

(57) ABSTRACT
A therapeutic agent delivery system includes a therapeutic agent delivery assembly carried by a housing. The therapeutic agent delivery assembly includes a chamber including a first passageway, a therapeutic agent carried in the first passageway, and a needle in communication with the first
(Continued)

passageway. The therapeutic agent delivery assembly is translatable relative to the housing from a stowed configuration to a deployed configuration. The therapeutic agent delivery assembly is also translatable relative to the housing from the deployed configuration to a retracted configuration. The system further includes a user input that is actuatable to translate the therapeutic agent delivery assembly from the stowed configuration to the deployed configuration. The system further includes a retraction mechanism that is actuatable to translate the therapeutic agent delivery assembly from the deployed configuration to the retracted configuration.

18 Claims, 27 Drawing Sheets

(58) Field of Classification Search
USPC ......................................................... 604/181
See application file for complete search history.

(56) References Cited

FOREIGN PATENT DOCUMENTS

| WO | 2018/142106 | 8/2018 |
| WO | 2019/023053 | 1/2019 |
| WO | 2019/118261 | 6/2019 |
| WO | 2020/131552 | 6/2020 |
| WO | 2020/131577 | 6/2020 |

OTHER PUBLICATIONS

Written Opinion of the International Searching Authority pertaining to International Application No. PCT/US2021/048576; Date of Mailing: Dec. 14, 2021; 7 pages.

* cited by examiner

146

DEVICES AND PROCESSES FOR DELIVERY OF THERAPEUTIC FLUIDS

FIELD OF THE DISCLOSURE

The present disclosure relates to processes and devices for parenteral delivery of therapeutic agents. More particularly, the present disclosure relates to processes and devices for parenteral delivery of high-viscosity therapeutic fluids (for example, protein therapeutics).

BACKGROUND OF THE DISCLOSURE

Protein therapeutics is an emerging class of drug therapy that provides treatment for a broad range of diseases, such as autoimmune disorders, cardiovascular diseases, diabetes, and cancer. A common delivery method for some protein therapeutics, such as monoclonal antibodies, is through intravenous infusion, in which large volumes of dilute solutions are delivered over time. Intravenous infusion usually requires the supervision of a doctor or nurse and is performed in a clinical setting. This can be inconvenient for a patient, and so efforts are being made to permit the delivery of protein therapeutics at home. Desirably, a protein therapeutic formulation can be administered using a syringe for subcutaneous delivery instead of requiring intravenous administration. Subcutaneous injections are commonly administered by laypersons, for example in the administration of insulin by diabetics.

Transitioning therapeutic protein formulations from intravenous delivery to injection devices like syringes and injection pens requires addressing challenges associated with delivering high concentrations of high molecular weight molecules in a manner that is easy, reliable, and causes minimal pain to the patient. In this regard, while intravenous bags typically have a volume of 1 liter, the standard volume for a syringe ranges from 0.3 milliliters up to 25 milliliters. Thus, depending on the drug, to deliver the same amount of therapeutic proteins, the concentration may have to increase by a factor of 40 or more. Also, injection therapy is moving towards smaller needle diameters and faster delivery times for purposes of patient comfort and compliance.

Delivery of protein therapeutics is also challenging because of the high viscosity associated with such therapeutic formulations, and the high forces needed to push such formulations through a parenteral device. Formulations with absolute viscosities above 40-60 centipoise (cP) may be difficult to deliver by conventional spring driven auto-injectors for multiple reasons. Structurally, the footprint of a spring for the amount of pressure delivered is relatively large and fixed to specific shapes, which reduces flexibility of design for delivery devices. Next, auto-injectors are usually made of plastic parts. However, a large amount of energy must be stored in the spring to reliably deliver high-viscosity fluids. If not properly designed, this stored energy may cause damage to the plastic parts due to creep, which is the tendency of the plastic part to permanently deform under stress. An auto-injector typically operates by using the spring to push a needle-containing internal component towards an outer edge of the housing of the syringe. The sound associated with the operation of a spring-based auto-injector may cause patient anxiety, potentially reducing future compliance. The generated pressure versus time profile of such a spring driven auto-injector cannot be readily modified, which prevents users from fine tuning pressure to meet their delivery needs.

It would be desirable to provide processes and devices by which a therapeutic fluid, in particular a high-viscosity fluid, could be self-administered in a reasonable time and with a limited injection space. These processes and devices could be used to deliver high-concentration protein, high-viscosity pharmaceutical formulations, or other therapeutic fluids.

SUMMARY

According to an embodiment of the present disclosure, a therapeutic agent delivery system includes a housing having a distal end portion. The system further includes a therapeutic agent delivery assembly carried by the housing. The therapeutic agent delivery assembly includes a chamber including a first passageway, a therapeutic agent carried in the first passageway, and a needle in communication with the first passageway. The therapeutic agent delivery assembly is translatable relative to the housing from a stowed configuration to a deployed configuration. In the deployed configuration, the needle at least partially extending distally from the distal end portion of the housing. The therapeutic agent delivery assembly is also translatable relative to the housing from the deployed configuration to a retracted configuration. In the retracted configuration, the needle is disposed proximally relative to the distal end portion of the housing. The system further includes a user input that is configured to be actuated by a user. Actuation of the user input translates the therapeutic agent delivery assembly from the stowed configuration to the deployed configuration. The system further includes a retraction mechanism that is actuatable to translate the therapeutic agent delivery assembly from the deployed configuration to the retracted configuration. The retraction mechanism includes a first chamber, a fluid carried in the first chamber, an inflatable device including a second chamber, and a valve that is actuatable from a closed position to an open position. In the closed position, the valve inhibits fluid communication between the first chamber and the second chamber. In the open position, the valve permits fluid communication between the first chamber and the second chamber such that the first chamber delivers the fluid to the second chamber. The inflatable device thereby inflates and translates the therapeutic agent delivery assembly from the deployed configuration to the retracted configuration.

According to another embodiment of the present disclosure, a therapeutic agent delivery system includes a housing having a distal end portion. The system further includes a therapeutic agent delivery assembly carried by the housing. The therapeutic agent delivery assembly includes a chamber including a first passageway, a therapeutic agent carried in the first passageway, and a needle in communication with the first passageway. The therapeutic agent delivery assembly is translatable relative to the housing from a stowed configuration to a deployed configuration. In the deployed configuration, the needle at least partially extends distally from the distal end portion of the housing. The therapeutic agent delivery assembly is translatable relative to the housing from the deployed configuration to a retracted configuration. In the retracted configuration, the needle is disposed proximally relative to the distal end portion of the housing. The system further includes a user input that is configured to be actuated by a user. Actuation of the user input translates the therapeutic agent delivery assembly from the stowed configuration to the deployed configuration. The system further includes a retraction mechanism that is actuatable to translate the therapeutic agent delivery assembly from the deployed configuration to the retracted configuration. The retraction mechanism includes a first chamber, a fluid carried in the first chamber, a second chamber, an electronics assembly configured to send a retraction signal, and a valve operably coupled to the electronics assembly. The valve is actuatable from a closed position to an open position upon receiving the retraction signal. In the closed position, the valve inhibits fluid communication between the first chamber and the second chamber. In the open position, the valve permits fluid communication between the first chamber and the second chamber such that the first chamber delivers the fluid to the second chamber. The retraction mechanism thereby translates the therapeutic agent delivery assembly from the deployed configuration to the retracted configuration.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The present disclosure relates to systems, devices, and processes for parenteral delivery of therapeutic agents, such as high-viscosity therapeutic fluids. Such systems and devices are illustratively provided with relatively compact profiles.

1. Drugs/Therapeutic Agents

Systems and devices according to the present disclosure may carry and facilitate delivery of a drug to a subject. The term "drug" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, combined GIP/GLP-1 agonists such as tirzepatide, oxyntomodulin analogs, oxyntomodulin derivatives, therapeutic antibodies and any therapeutic agent that is capable of delivery by devices according to the present disclosure. The drug may be formulated with one or more excipients. Devices according to the present disclosure are operated in a manner generally as described herein by a patient, caregiver or healthcare professional to deliver a drug to a subject.

In certain embodiments, a therapeutic agent is protein, such as a monoclonal antibody or some other protein which is therapeutically useful. In some embodiments, the protein may have a concentration of from about 75 mg/mL to about 500 mg/mL in a fluid. In certain embodiments, the protein may have a concentration of about 150 mg/mL, 200 mg/mL, 250 mg/mL, or more. A drug may further contain a solvent or non-solvent, such as water, perfluoroalkane solvent, safflower oil, or benzyl benzoate.

A drug may be a fluid, more specifically a high-viscosity fluid and may have an absolute viscosity of from about 5 cP to about 1000 cP. In certain embodiments, a high-viscosity fluid has an absolute viscosity of at least about 10 cP, 20 cP, 30 cP, 40 cP, 50 cP, 60 cP, or more.

2. Therapeutic Agent Delivery System

Figure 1:
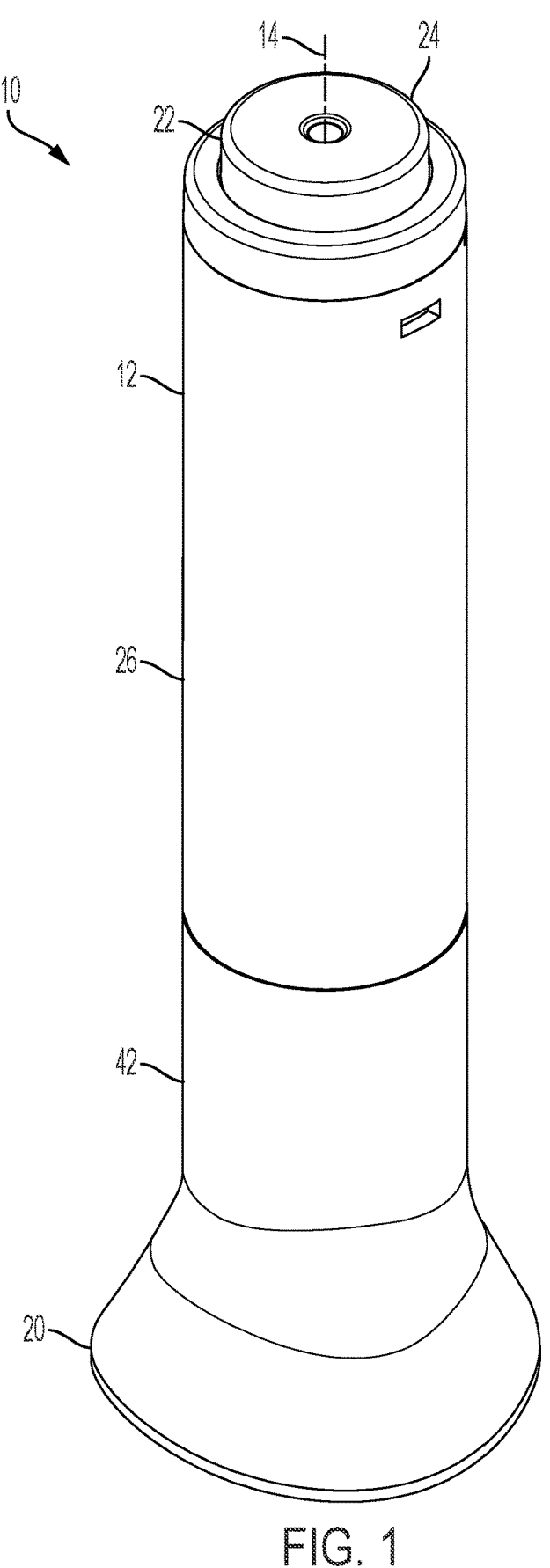
FIG. 1 is a top perspective view of a therapeutic agent delivery system according to an embodiment of the present disclosure.
Figure 2:
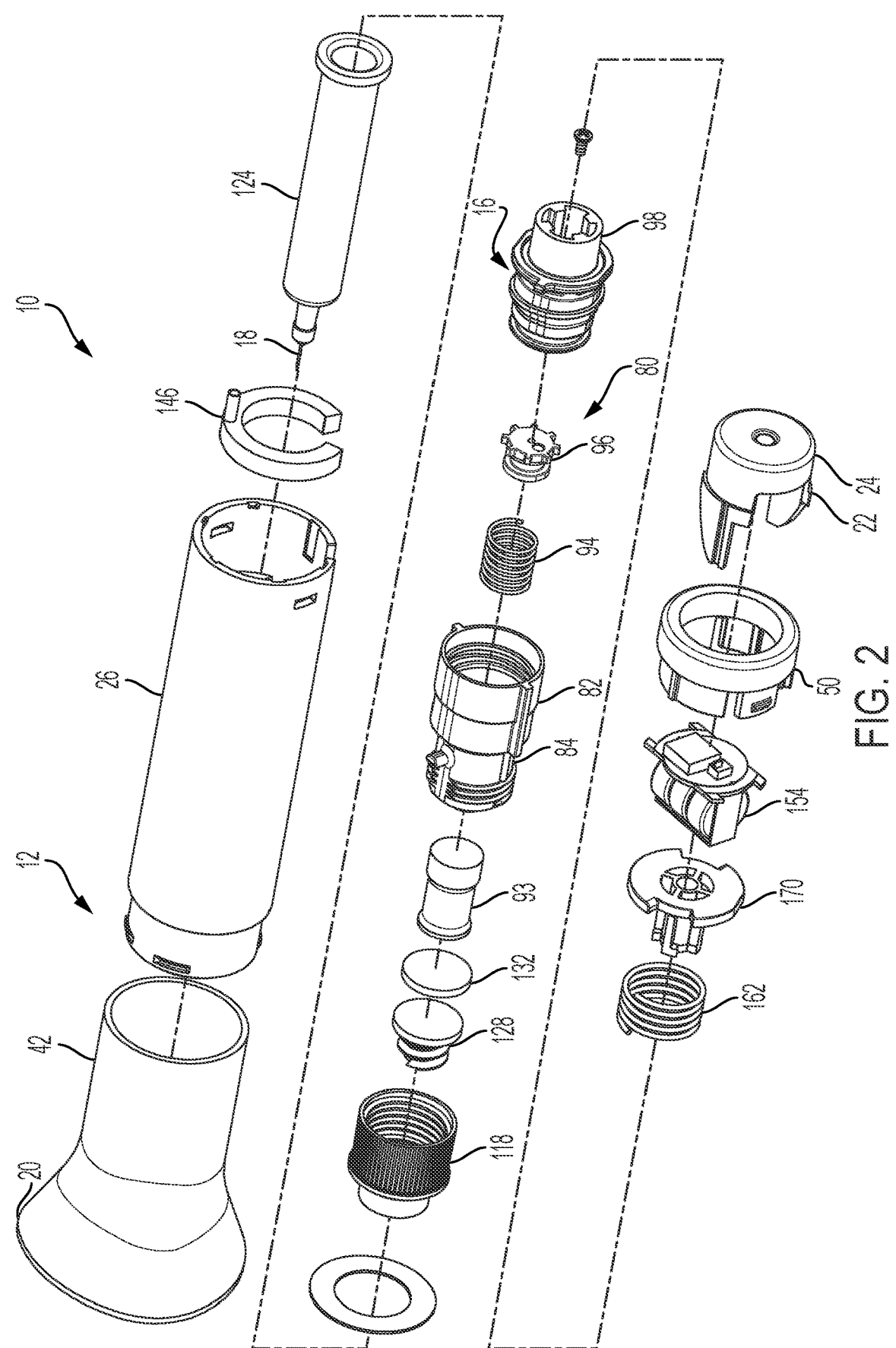
FIG. 2 is a partially exploded view of the therapeutic agent delivery system of FIG. 1.
Figure 3:
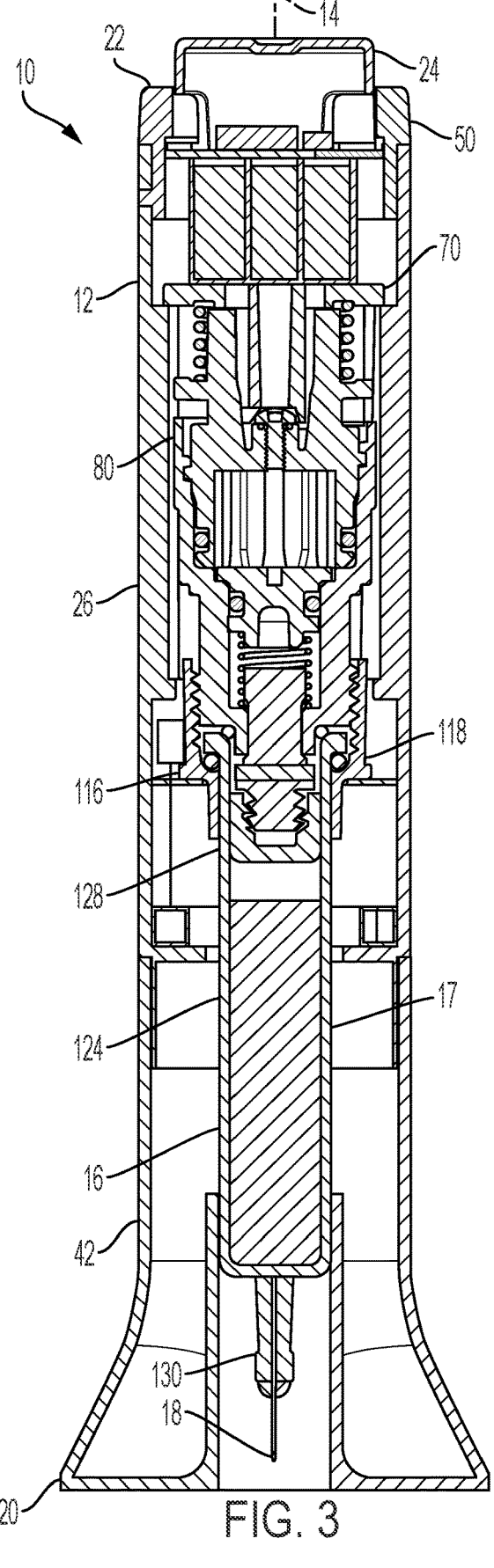
FIG. 3 is a longitudinal sectional view of the therapeutic agent delivery system of FIG. 1.

FIGS. 1-3 illustrate a therapeutic agent delivery system 10 according to an embodiment of the present disclosure. Illustratively, the therapeutic agent delivery system 10 generally includes the profile of an auto-injector pen, although other profiles may alternatively be used. Generally, the therapeutic agent delivery system 10 includes a housing 12 that is elongated along a longitudinal axis 14. The housing 12 carries a therapeutic agent delivery assembly 16. The therapeutic agent delivery assembly 16 includes a therapeutic agent 17 (see FIG. 3) and a needle 18, and the therapeutic agent delivery assembly 16 translates relative to the housing 12 from a stowed configuration (as illustratively shown in FIGS. 1-3, a configuration in which the needle 18 is disposed entirely within the housing 12) to a deployed configuration (shown elsewhere—for example, a configuration in which the needle 18 is at least partially exposed at a distal end portion 20 of the housing 12 and configured to engage the subject and deliver the therapeutic agent to the subject). A proximal end portion 22 of the therapeutic agent delivery system 10 includes a user input 24 (illustratively, a depressible button) that is actuated to actuate the therapeutic agent delivery assembly 16 (that is, move the needle 18 from the stowed configuration to the deployed configuration and deliver the therapeutic agent to the user). After actuation, the therapeutic agent delivery assembly 16 translates relative to the housing 12 from the deployed configuration to a retracted configuration (shown elsewhere—for example, a configuration in which the needle 18 is disposed entirely within the therapeutic agent delivery system 10). The therapeutic agent delivery system 10 includes a retraction mechanism (shown elsewhere) that translates the therapeutic agent delivery assembly 16 relative to the housing 12 from the deployed configuration to the retracted configuration. After reaching the retracted configuration, the therapeutic agent delivery assembly 16 is inhibited from being translated to the deployed configuration (stated another way, the system 10 is "locked out"). These aspects, features, and components of the therapeutic agent delivery system 10 are described in further detail below.

Figure 4:
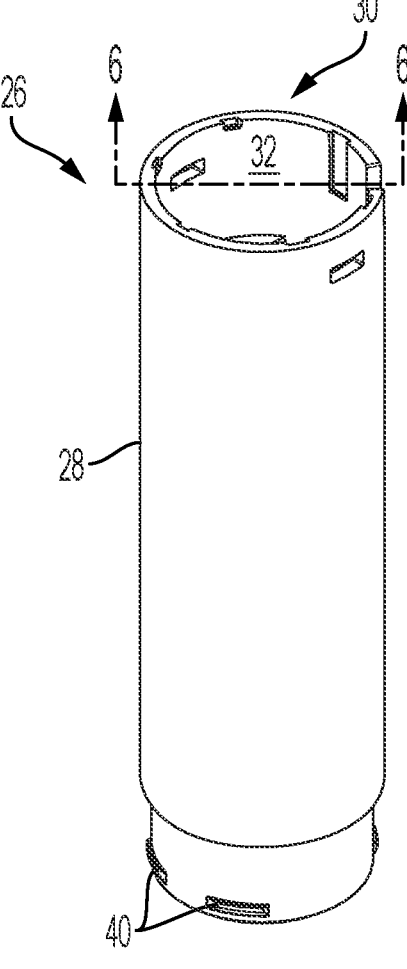
FIG. 4 is a top perspective view of a proximal housing portion of a housing of the therapeutic agent delivery system of FIG. 1.
Figure 5:
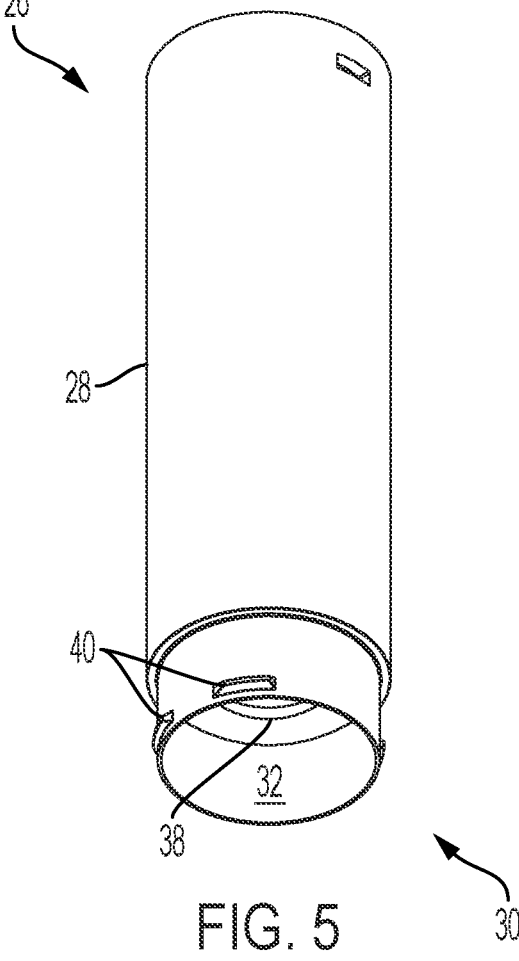
FIG. 5 is a bottom perspective view of the proximal housing portion of FIG. 4.
Figure 6:
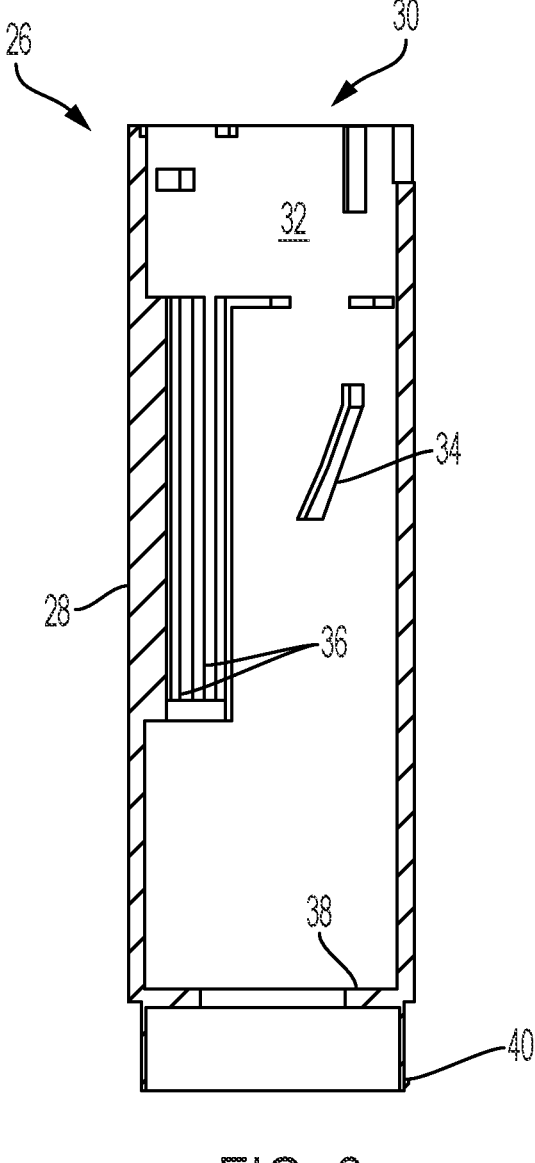
FIG. 6 is a longitudinal sectional view of the proximal housing portion along line 6-6 of FIG. 4.

FIGS. 4-6 illustrate a proximal housing portion 26 of the housing 12. The proximal housing portion 26 includes a main body 28 that has a generally cylindrical shape. The main body 28 includes an inner passageway 30 that carries other components of the therapeutic agent delivery system 10. Adjacent to the inner passageway 30, an inner surface 32 of the proximal housing portion 26 carries an actuation feature (illustratively, two helically extending ramps 34, one of which is shown in FIG. 6) that, as described in further detail below, selectively engage and facilitate actuating the therapeutic agent delivery assembly 16. The inner surface 32 of the proximal housing portion 26 carries translation features (illustratively, two pairs of axially extending ridges 36, one pair of which is shown in FIG. 6) that facilitate translation of the therapeutic agent delivery assembly 16 relative to the proximal housing portion 26. The inner surface 32 also carries a biasing platform (illustratively, a radially-inwardly extending flange 38) that, as described in further detail below, carries other components and facilitates translating the therapeutic agent delivery assembly 16 from the deployed configuration to the retracted configuration. The proximal housing portion 26 includes a coupling feature (illustratively, a plurality of snap connectors 40) for coupling to another portion of the housing 12.

Figure 7:
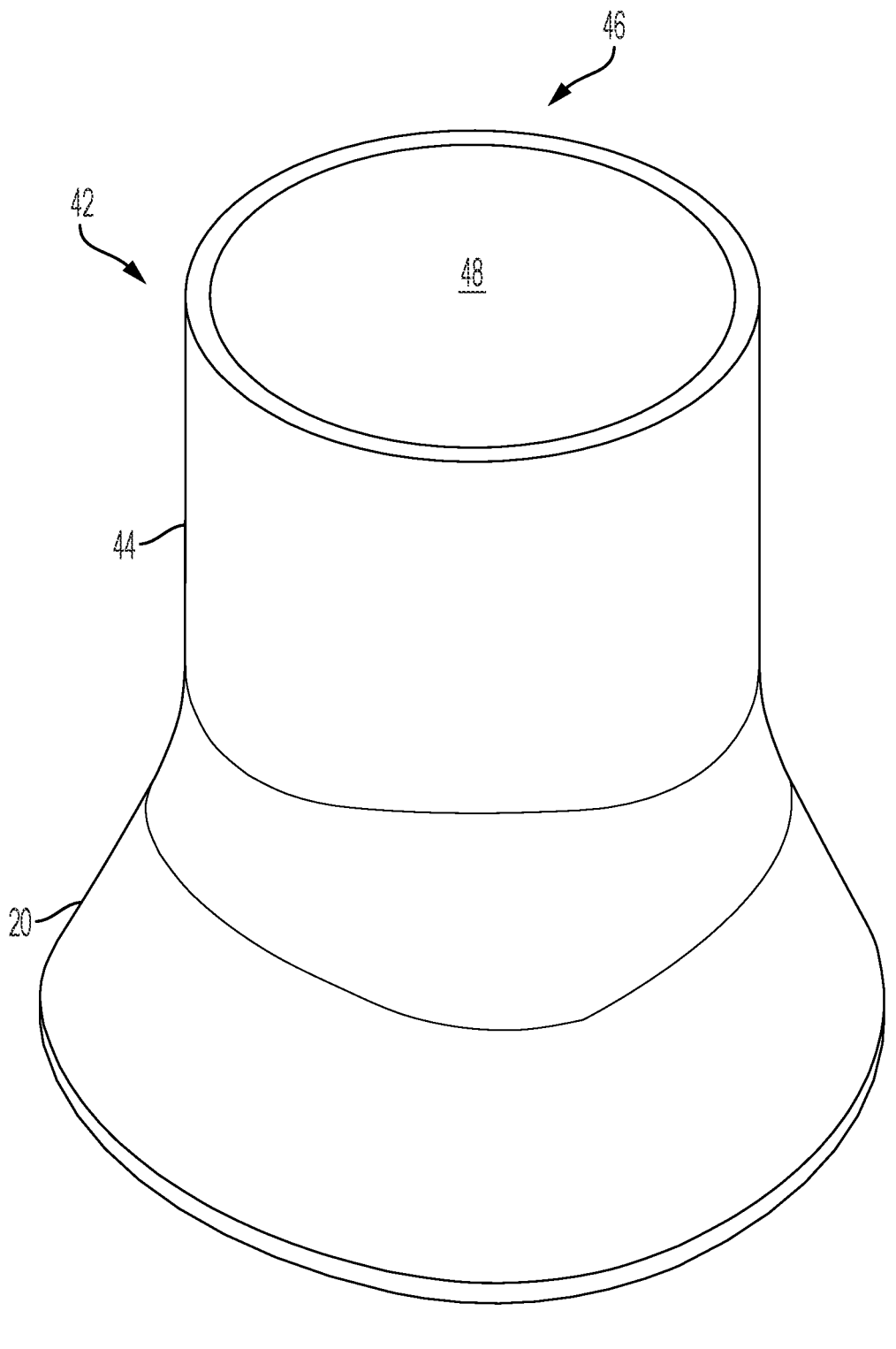
FIG. 7 is a top perspective view of a distal housing portion of the housing of the therapeutic agent delivery system of FIG. 1.
Figure 8:
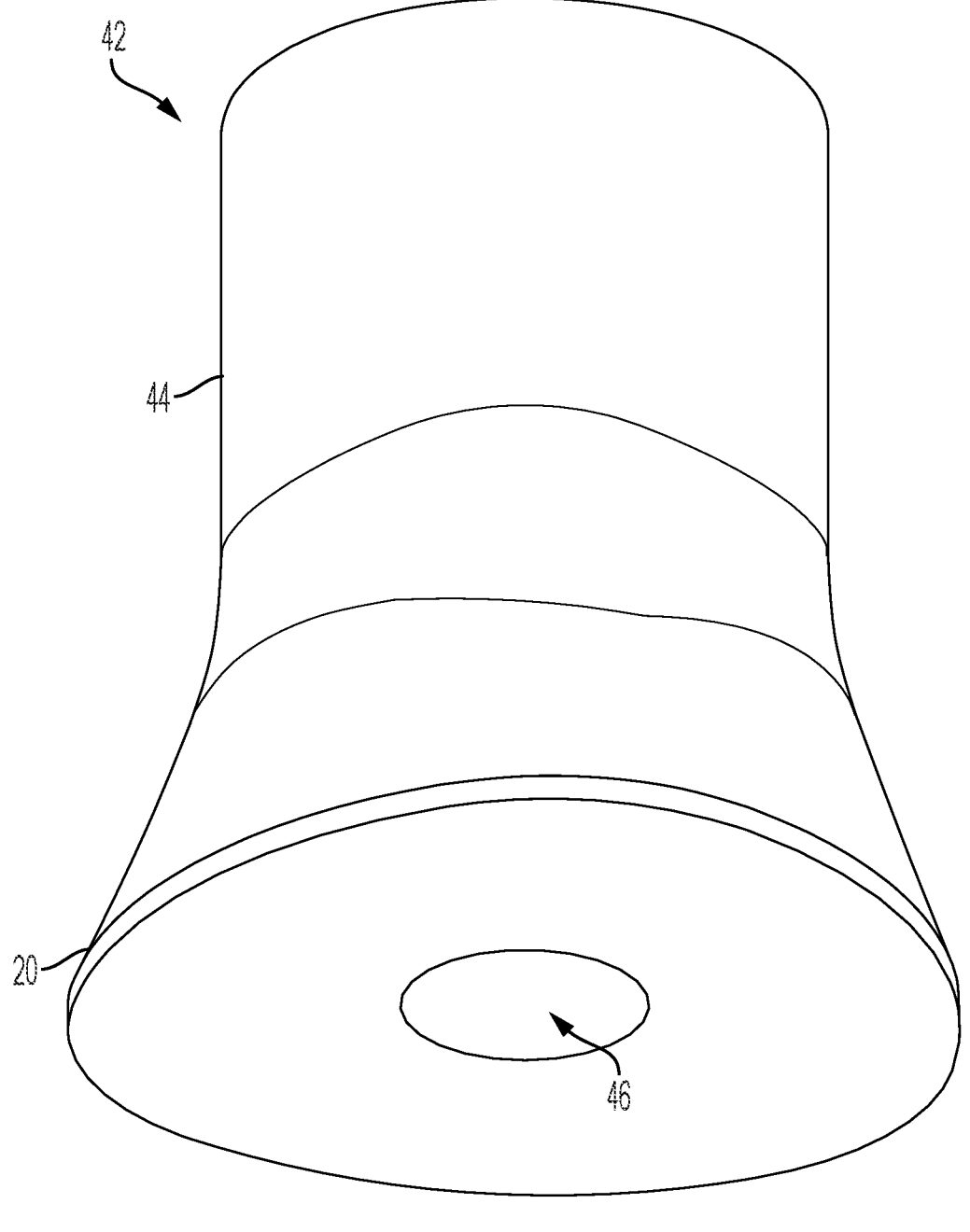
FIG. 8 is a bottom perspective view of the distal housing portion of FIG. 7.

FIGS. 7 and 8 illustrate a distal housing portion 42 of the housing 12. The distal housing portion 42 includes a main body 44 that has a generally conical shape with a flared distal end portion 20. The main body 44 includes an inner passageway 46 that carries the therapeutic agent delivery assembly 16 (shown elsewhere). The distal housing portion 42 also includes a coupling feature (illustratively, an inner surface 48 of the inner passageway 46) for coupling to the coupling feature of the proximal housing portion 26 (shown elsewhere—illustratively, the plurality of snap connectors 40). In other embodiments, different arrangements of the distal housing portion 42 are possible. For example, the distal housing portion 42 may be monolithically formed with the proximal housing portion 26.

Figure 9:
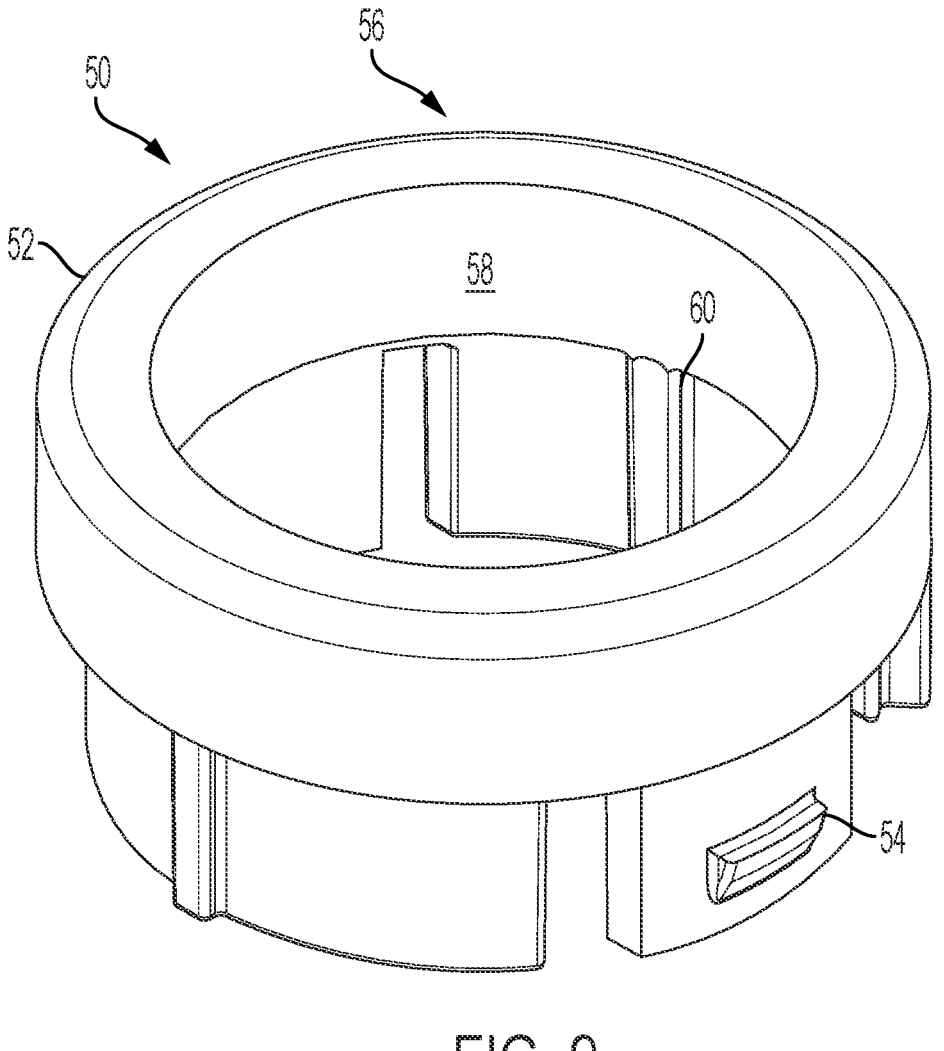
FIG. 9 is a top perspective view of a user input support of the therapeutic agent delivery system of FIG. 1.

FIG. 9 illustrates a user input support 50 of the therapeutic agent delivery system 10. The user input support 50 couples to the proximal housing portion 26 opposite the distal housing portion 42 (both shown elsewhere). The user input support 50 includes a main body 52, and the main body 52 carries a coupling feature (illustratively, a plurality of snap connectors 54, one of which is shown in FIG. 9) for coupling to the proximal housing portion 26. The main body 52 includes an inner passageway 56 that receives the user input 24 (shown elsewhere). Adjacent to the inner passageway 56, an inner surface 58 of the user input support 50 carries a translation feature (illustratively, a plurality of axially extending ridges 60, one of which is shown in FIG. 9) that facilitates translation of the user input 24 relative to the user input support 50. In other embodiments, different arrangements of the user input support 50 are possible.

Figure 10:
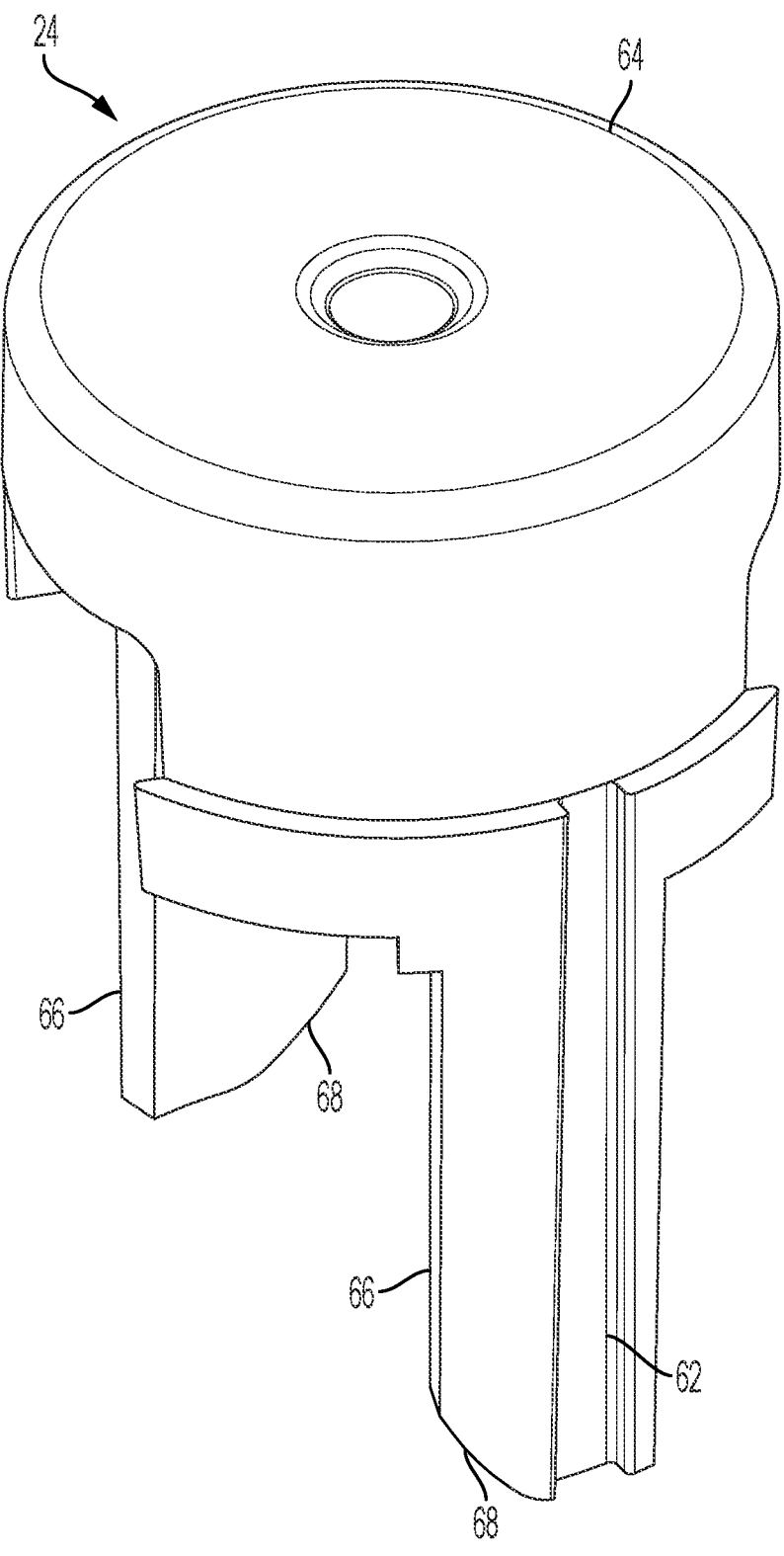
FIG. 10 is a top perspective view of a user input of the therapeutic agent delivery system of FIG. 1.

FIG. 10 illustrates the user input 24 of the therapeutic agent delivery system 10. The user input 24 includes a translation feature (illustratively, a plurality of axially extending channels 62, one of which is shown in FIG. 10) for engaging the translation feature of the user input support 50 (shown elsewhere—illustratively, the plurality of axially extending ridges 60) to facilitate translation of the user input 24 relative to the user input support 50 and the housing 12 (shown elsewhere). Adjacent to the translation feature, the user input 24 includes an exposed portion 64 that is pressed by a user to translate the user input 24 relative to the user input support 50 and the housing 12. The user input 24 also includes an actuation feature that facilitates actuating the therapeutic agent delivery assembly 16. Illustratively, the actuation feature includes two arms 66 that are disposed opposite the exposed portion 64. Each of the arms 66 includes an actuation surface (illustratively, a helically extending surface 68). Interaction of the arms 66 with other components of the therapeutic agent delivery system 10 is described in further detail below. In other embodiments, different arrangements of the user input 24 are possible.

Figure 11:
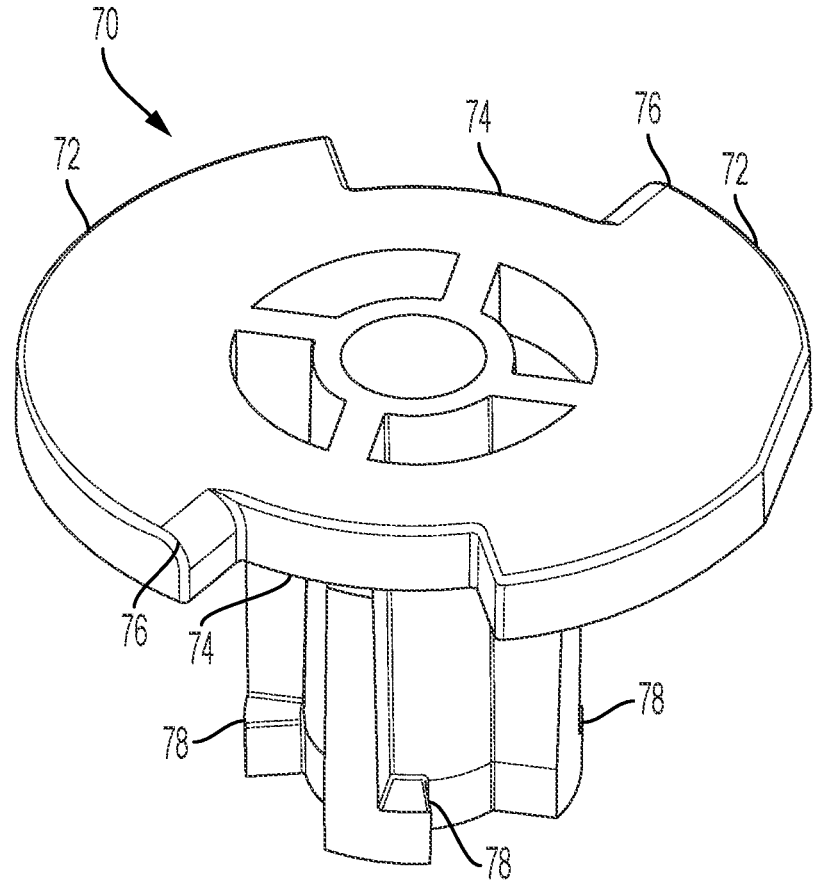
FIG. 11 is a top perspective view of an input drive of the therapeutic agent delivery system of FIG. 1.
Figure 12:
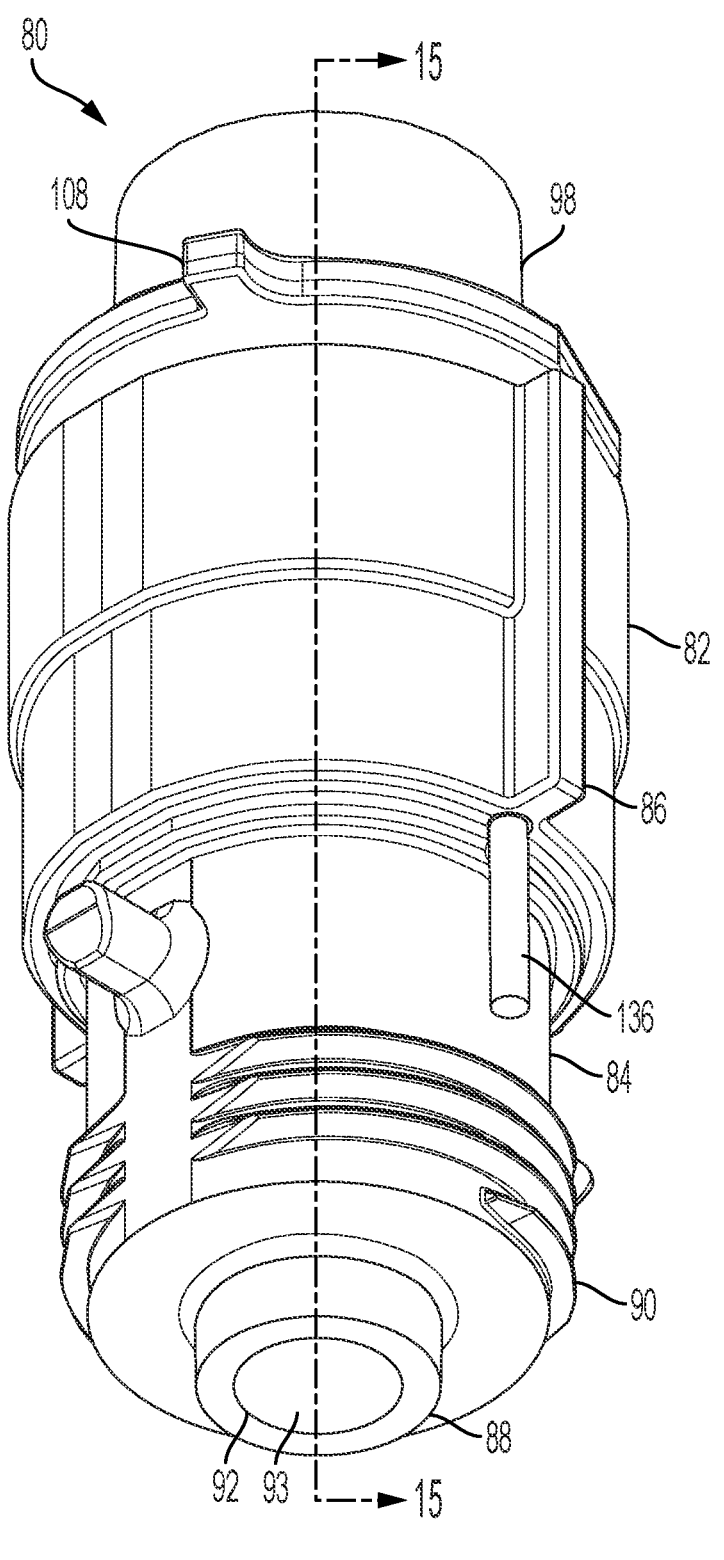
FIG. 12 is a bottom perspective view of a pressure generating actuator of a therapeutic agent delivery assembly of the therapeutic agent delivery system of FIG. 1.
Figure 13:
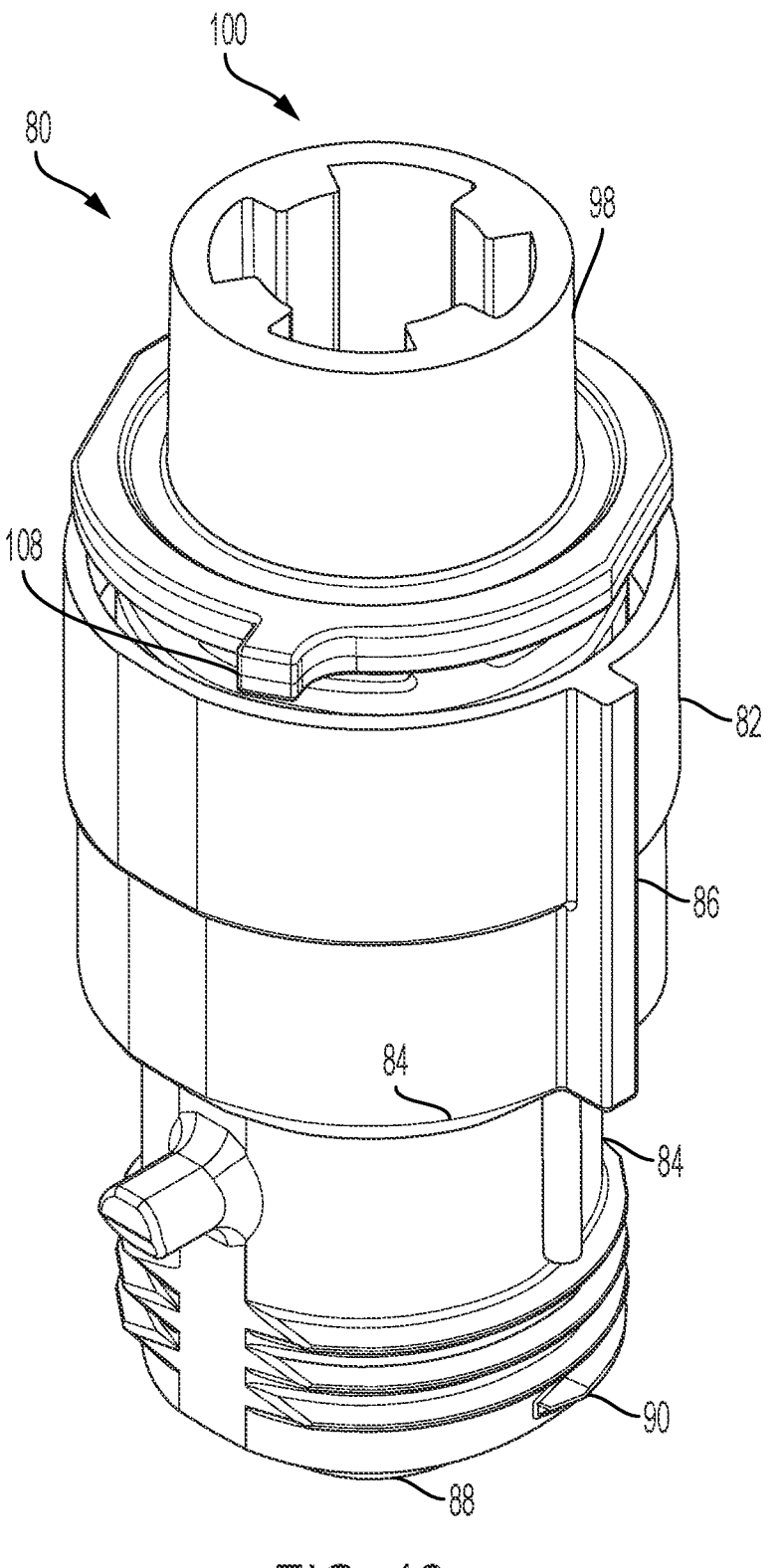
FIG. 13 is a top perspective view of the pressure generating actuator of FIG. 12.
Figure 14:
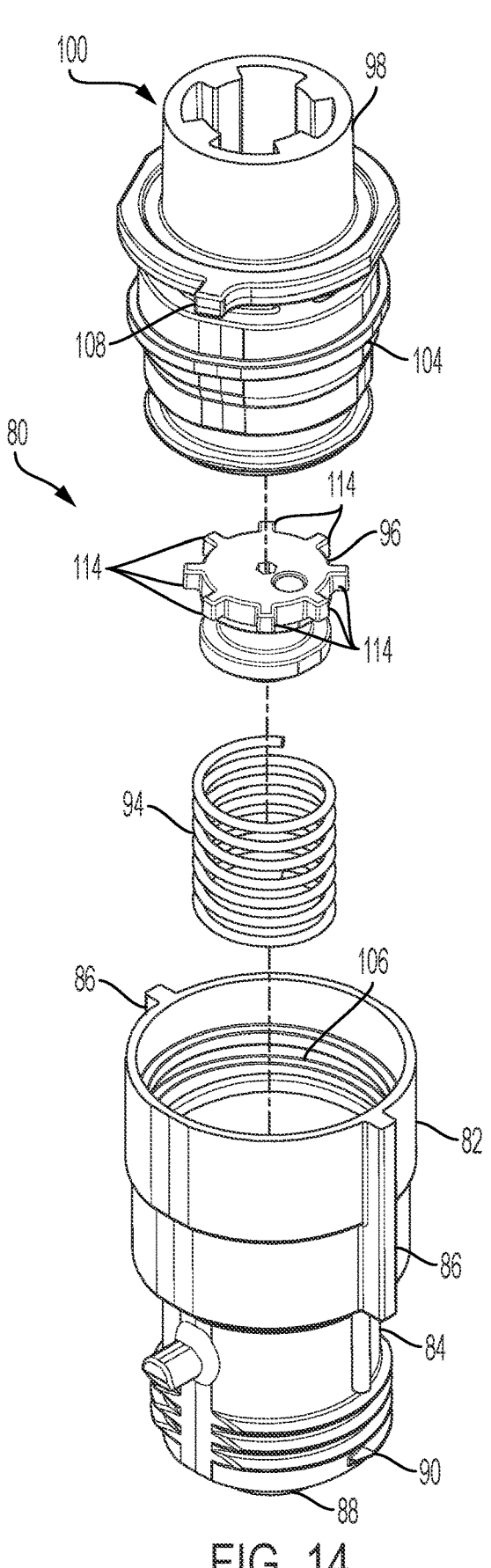
FIG. 14 is a partially exploded perspective view of the pressure generating actuator of FIG. 12.

FIG. 11 illustrates an input drive 70 of the therapeutic agent delivery system 10. The input drive 70 includes an actuation feature that is configured to interact with the actuation feature of the user input 24 (shown elsewhere). Illustratively, the actuation feature of the input drive 70 includes two partial flanges 72 and two openings 74 disposed between the partial flanges 72. Each of the partial flanges 72 includes an actuation surface (illustratively, a rounded corner 76 adjacent to one of the openings 74) that engages one of the actuation surfaces 68 of the user input 24 to facilitate rotating the input drive 70 relative to the housing 12 (shown elsewhere) upon translating the user input 24 relative to the housing 12. Opposite the actuation feature, the input drive 70 includes a detachable coupling feature (illustratively, a plurality of ledges 78 or radially-outwardly extending L-shaped protrusions 78) that detachably couples the input drive 70 to the therapeutic agent delivery assembly 16 (shown elsewhere). In other embodiments, different arrangements of the input drive 70 are possible.

FIGS. 12-15 illustrate a pressure generating actuator 80 of the therapeutic agent delivery assembly 16 and fluid passageway 136 (see FIG. 12), which is described in further detail below. Generally, the pressure generating actuator 80 is actuated by the user input 24, via the input drive 70 (both shown elsewhere), to facilitate mixing of internally-carried chemical reagents, which generates one or more pressurized fluids (for example, one or more gases). Examples of suitable reagents and generated gases are provided below. As described in further detail below, the pressurized fluid(s) are delivered to and facilitate movement of other components of the therapeutic agent delivery assembly 16 (shown elsewhere).

The pressure generating actuator 80 includes a first mixing chamber 82 and a second mixing chamber 84, which are illustratively monolithically formed with each other. Externally, the first mixing chamber 82 and the second mixing chamber 84 include translation features (illustratively, two axially extending ridges 86) for translatably coupling to the translation features of the proximal housing portion 26 (shown elsewhere—illustratively, each of the axially extending ridges 86 is translatably received by one of the pairs of axially extending ridges 36 of the proximal housing portion 26). As a result, the pressure generating actuator 80 is translatably carried by the proximal housing portion 26. At an outlet end portion 88, the mixing chambers 82, 84 include an outlet coupling feature (illustratively, an externally threaded surface 90) for coupling to another component of the therapeutic agent delivery assembly 16. The outlet end portion 88 also includes an actuator outlet 92 (illustratively shown as carrying an absorbent material 93, as described in further detail below). Pressurized fluid is discharged from the pressure generating actuator 80 via the outlet 92.

Figure 15:
FIG. 15 is a longitudinal sectional view of the pressure generating actuator along line 15-15 of FIG. 12.
Figure 19:
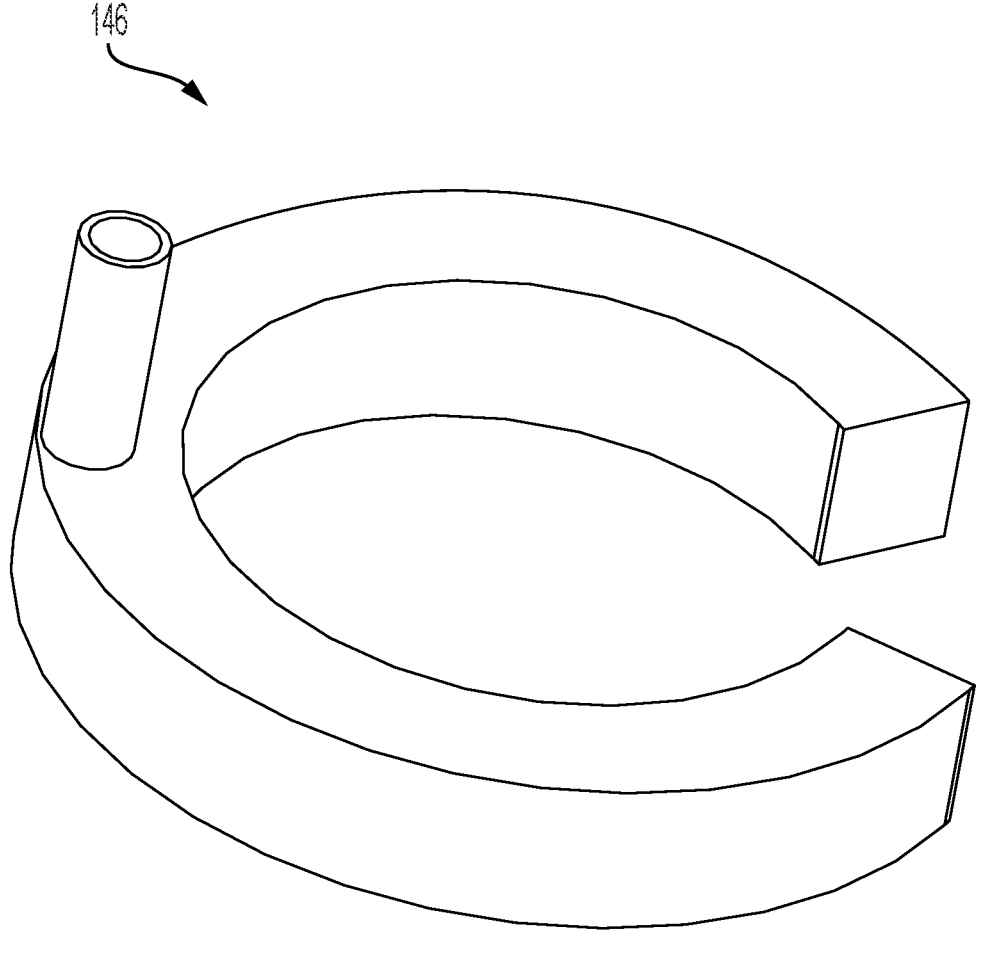
FIG. 19 is a top perspective view of an inflatable device of the therapeutic agent delivery system of FIG. 1.

Internally, the mixing chambers 82, 84 carry an actuator spring 94, a mixing piston 96, and a rotatable shuttle 98 in an axially stacked arrangement. The rotatable shuttle 98 includes a recess 100, and the recess 100 carries a detachable coupling feature (illustratively, a plurality of ledges 102 or radially-outwardly extending L-shaped protrusions 102, one of which is shown in FIG. 15) that engages the detachable coupling feature of the input drive 70 (illustratively, the plurality of ledges 78). The first mixing chamber 82 and the shuttle 98 form a helical coupling for movably coupling to each other. Illustratively, the shuttle 98 includes a helically extending ridge 104 and the first mixing chamber 82 includes a helically extending groove 106 that receives the ridge 104. The shuttle 98 includes an actuation feature (illustratively, two radially-outwardly extending fingers 108) that, as described in further detail below, engage and are driven by the actuation feature of the proximal housing portion 26 (shown elsewhere—illustratively, the two helically extending ramps 34). Internally, the shuttle 98 includes a first restraining feature (illustratively, eight radially-inwardly extending tabs 110, four of which are identified in FIG. 15) that engages the mixing piston 96. Illustratively, the shuttle 98 also includes channels 112 (three of which are identified in FIG. 15) disposed between adjacent tabs 110. The mixing piston 96 includes a second restraining feature (illustratively, eight radially-outwardly extending tabs 114) that engages the first restraining feature of the shuttle 98. Initially and as shown in FIG. 19, the first restraining feature engages the second restraining feature (illustratively, the radially-inwardly extending tabs 110 of the shuttle 98 are angularly aligned with and engage the radially-outwardly extending tabs 114 of the mixing piston 96) to hold the mixing piston 96 in a position between the first mixing chamber 82 and the second mixing chamber 84. The mixing piston 96 thereby maintains separation of reagents in the first mixing chamber 82 and the second mixing chamber 84. Initially the actuator spring 94 is also compressed within the second mixing chamber 84 against the mixing piston 96. In a subsequent configuration, as described in further detail below, the shuttle 98 rotates relative to the first mixing chamber 82 and the second mixing chamber 84 to disengage the first restraining feature from the second restraining feature (illustratively, the radially-inwardly extending tabs 110 of the shuttle 98 are angularly misaligned with, or angularly offset from, the radially-outwardly extending tabs 114 of the mixing piston 96, and the channels 112 are angularly aligned with the radially-outwardly extending tabs 114 of the mixing piston 96). As a result, the actuator spring 94 expands and moves the mixing piston 96 into the shuttle 98 and the first mixing chamber 82, which permits the reagents in the first mixing chamber 82 and the second mixing chamber 84 to mix. Mixing of the reagents generates one or more pressurized fluids (for example, one or more gases), and the pressurized fluid(s) are delivered to other components of the therapeutic agent delivery assembly 16.

In some embodiments, pressure generating actuators 80 have different structures. For example, suitable pressure generating actuators 80 include those described in: U.S. Pat. No. 9,795,740 titled "Chemical Engines and Methods for Their Use, Especially in the Injection of Highly Viscous Fluids"; U.S. Publication No. 2020/0030537, titled "Processes and Devices for Delivery of Fluid by Chemical Reaction"; and International Publication No. WO2019/050791, titled "System for Controlling Gas Generation with a Drug Delivery Device", the disclosures of which are expressly incorporated herein by reference in their entireties.

Any suitable chemical reagent or reagents can be used to generate one or more pressurized fluids in pressure generating actuators 80 of the present disclosure. Examples of generated gases include carbon dioxide gas, nitrogen gas, oxygen gas, chlorine gas, etc. Desirably, the generated gas is inert and non-flammable. The amount of gas needed to facilitate movement of other components of the therapeutic agent delivery assembly 16 may impact the type, amount, and concentration of each reagent used in pressure generating actuators 80. The reagents may be in dry form (for example, powdered form, tablet form) and/or in liquid form.

In one exemplary embodiment, a bicarbonate (which may be present in dry form) reacts with an acid (which may be present in liquid form) to produce carbon dioxide gas in pressure generating actuators 80. Examples of suitable bicarbonates include sodium bicarbonate, potassium bicarbonate, and ammonium bicarbonate. Other ingredients may also be present along with the bicarbonates, such as diatomaceous earth. Examples of suitable acids include acetic acid, citric acid, potassium bitartrate, disodium pyrophosphate, and calcium dihydrogen phosphate. In one particular example, the bicarbonate is potassium bicarbonate and the acid is aqueous citric acid, which may react to produce carbon dioxide gas and a liquid mixture of water and dissolved potassium citrate.

In some embodiments, other reactions may be used. In one example, a metal carbonate, such as copper carbonate or calcium carbonate, is thermally decomposed to produce carbon dioxide gas and the corresponding metal oxide in pressure generating actuators 80. In another example, 2,2'-azobisisobutyronitrile (AIBN) is heated to produce nitrogen gas in pressure generating actuators 80. In yet another example, enzymes (for example yeast) are reacted with sugar to produce carbon dioxide gas in pressure generating actuators 80. Some substances readily sublime, going from solid to gas. Such substances include but are not limited to naphthalene and iodine. In still yet another example, hydrogen peroxide is decomposed with catalysts such as enzymes (for example catalase) or manganese dioxide to produce oxygen gas in pressure generating actuators 80. In still yet another example, silver chloride is decomposed through exposure to light to generate a gas in pressure generating actuators 80. Suitable reagents, chemical formulations, and reactions are further described in the above-incorporated U.S. Pat. No. 9,795,740, U.S. Publication No. 2020/0030537, and International Publication No. WO2019/050791.

As described briefly above, the outlet 92 of the pressure generating actuator 80 may carry one or more absorbent materials 93. Such absorbent materials 93 may absorb excess liquid provided by mixing the reagents within the pressure generating actuator 80. Suitable absorbent materials are further described in the above-incorporated U.S. Publication No. 2020/0030537.

Figure 16:
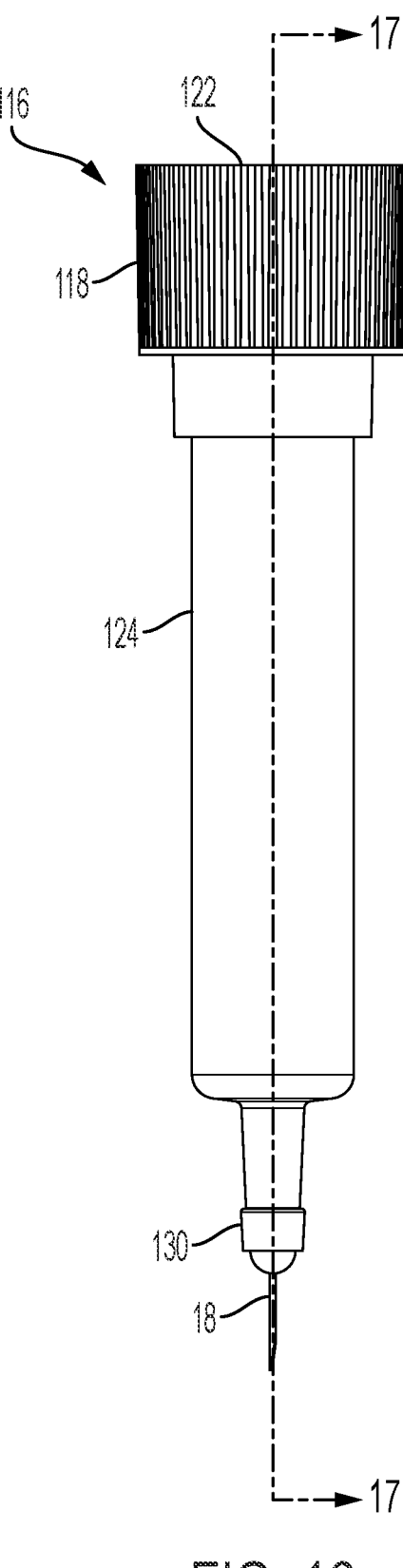
FIG. 16 is a side view of a syringe assembly of the therapeutic agent delivery assembly of the therapeutic agent delivery system of FIG. 1.
Figure 17:
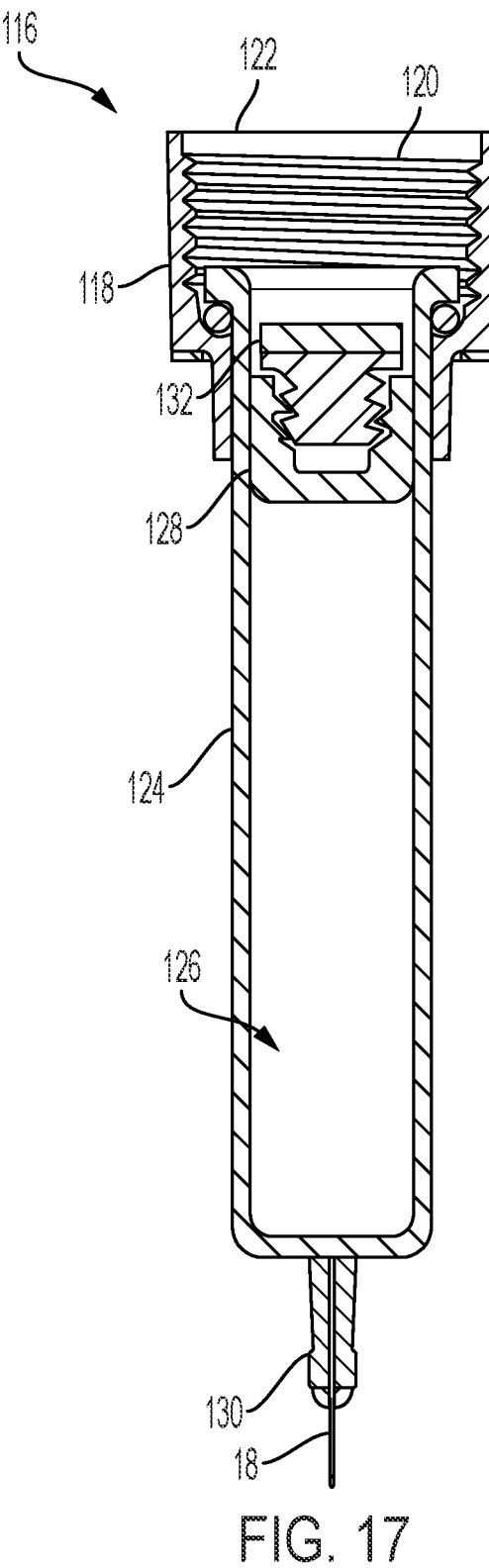
FIG. 17 is a longitudinal sectional view of the syringe assembly along line 17-17 of FIG. 16.

FIGS. 16 and 17 illustrate a syringe assembly 116 of the therapeutic agent delivery assembly 16. The syringe assembly 116 includes an inlet portion 118, and the inlet portion 118 includes an inlet coupling feature (illustratively, an internally threaded surface 120, as shown in FIG. 17) that couples to the outlet coupling feature of the pressure generating actuator 80 (shown elsewhere—illustratively, the externally threaded surface 90). The inlet portion 118 also includes an inlet 122 that receives pressurized fluid(s) from the outlet 92 of the pressure generating actuator 80. The inlet portion 118 couples to a syringe chamber 124, and the syringe chamber 124 includes a syringe passageway 126 that receives the pressurized fluid(s) from the inlet portion 118. The syringe passageway 126 carries a syringe piston 128, and the syringe piston 128 translates away from the inlet portion 118 and towards an outlet portion 130 of the syringe assembly 116 when the syringe passageway 126 receives the pressurized fluid(s). Illustratively and as described in further detail below, the syringe piston 128 carries a magnetic component 132, which may also be referred to as a target, that facilitates determining the position of the syringe piston 128 in the syringe passageway 126. The syringe passageway 126 also carries the therapeutic agent (shown elsewhere—illustratively, 2.25 mL of the therapeutic agent, although other volumes, including, for example, 0.5 mL, 1.0 mL, 3.0 mL, or 5.0 mL may alternatively be carried) between the syringe piston 128 and the outlet portion 130, more specifically the needle 18. As such, translation of the syringe piston 128 in the syringe passageway 126 causes the needle 18 to discharge the therapeutic agent therefrom. In other embodiments, different arrangements are possible. For example, the inlet portion 118 and the syringe chamber 124 may be monolithically formed with each other, or the syringe assembly 116 could be replaced by another type of therapeutic agent container, such as a bellows or bladder structure.

Beneath the inlet portion 118, the syringe assembly 116 includes a retraction surface (illustratively, a retraction ring 133 positioned between the inlet portion 118 and the syringe chamber 124 as shown in FIGS. 2 and 3).

Figure 18:
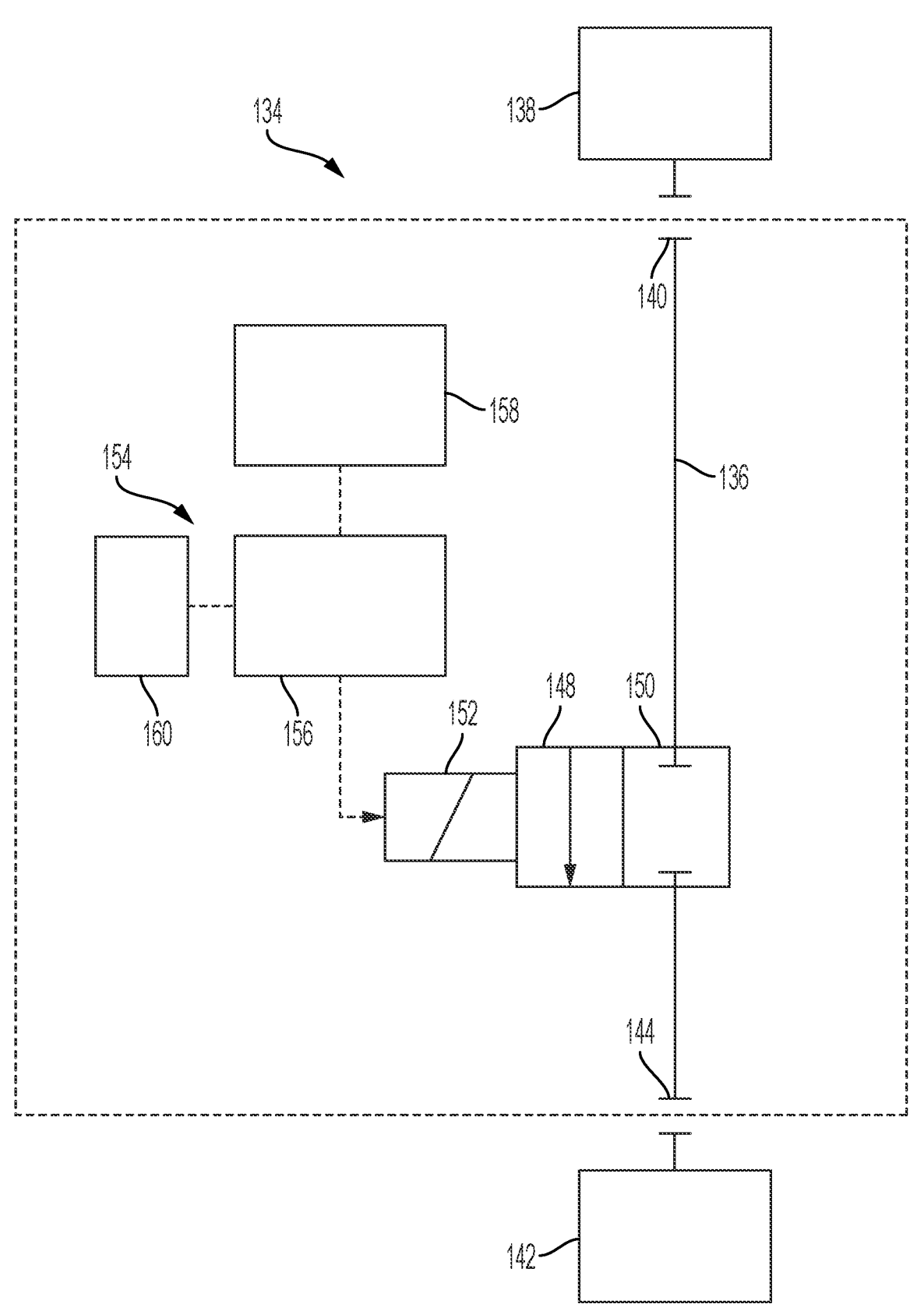
FIG. 18 is a schematic representation of a retraction mechanism of the therapeutic agent delivery system of FIG. 1.

FIG. 18 schematically illustrates a retraction mechanism 134 of the therapeutic agent delivery system 10. Generally, the retraction mechanism 134 is actuatable to translate the therapeutic agent delivery assembly 16 relative to the housing 12 (both shown elsewhere) from the deployed configuration to the retracted configuration. The retraction mechanism 134 includes a passageway 136 that couples to a first chamber 138 at a first end 140. The passageway 136 is in fluid communication with the first chamber 138 and receives a fluid therefrom. The first chamber 138 may include, for example, the second mixing chamber 84 of the therapeutic agent delivery assembly 16 (shown elsewhere) and the fluid may include, for example, the pressurized fluid(s) generated by the therapeutic agent delivery assembly 16, as described in further detail below. The passageway 136 also couples to a second chamber 142 at a second end 144. The passageway 136 is in fluid communication with the second chamber 142 and delivers the fluid thereto. As described in further detail below, the second chamber 142 receives the fluid to increase the volume of the second chamber 142 and thereby drive the therapeutic agent delivery assembly 16 relative to the housing 12 from the deployed configuration to the retracted configuration. The second chamber 142 may be part of, for example and as described in further detail below, an inflatable device (shown elsewhere).

The retraction mechanism 134 further includes a valve 148 for selectively permitting flow of the fluid from the first chamber 138 to the second chamber 142. Stated another way, the valve 148 is actuatable from a closed position to an open position. In the closed position, the valve 148 inhibits fluid communication between the first chamber 138 and the second chamber 142. In the open position, the valve 148 permits fluid communication between the first chamber 138 and the second chamber 142 such that the first chamber 138 delivers the fluid to the second chamber 142.

With continued reference to FIG. 18, the valve 148 includes a valve element 150 and a valve actuator 152. The valve element 150 is reconfigurable from the closed position to the open position to selectively inhibit and permit flow of the fluid, respectively, in the passageway 136. The valve actuator 152 actuates the valve element 150 from the closed position to the open position. The valve element 150 and the valve actuator 152 may take various forms. For example, the valve element 150 may include a frangible element, and the valve actuator 152 may actuate the valve element 150 by damaging or destroying the frangible element. As a more specific example, the valve element 150 may include a meltable element that initially disposed in the passageway 136, and the valve actuator 152 may include a heating element. In these embodiments, the valve actuator 152 actuates the valve element 150 by delivering heat from the heating element to the meltable element, and the heating element thereby melts the meltable element. As an even more specific example, the meltable element may include a wax plug, the heating element may be electrical conductors coupled to carbon nanotube paper or nichrome wire wrapped around the passageway 136 and the meltable element, and the passageway 136 may include a thermally conductive material, such as stainless steel. As alternatives, carbon nanotube paper or nichrome wire may be disposed within the passageway 136 and around the meltable element, or a wire may be disposed within the meltable element. As another alternative, the heating element may include electrical conductors coupled to the passageway 136, such that the passageway 136 itself acts as part of the heating element. In this alternative, the passageway 136 may include titanium, an austenitic nickel-chromium-based superalloy, other high-temperature alloys, or the like. As another example, the valve 148 may be an electromechanical valve, such as a solenoid valve. That is, the valve actuator 152 may include solenoid coils, and the valve element 150 may include a valve seat that is actuated by the solenoid coils to permit flow through a valve body.

With further reference to FIG. 18, the retraction mechanism 134 further includes an electronics assembly 154 that is operatively coupled to the valve 148. The electronics assembly 154 includes an electronic controller 156 that is operatively coupled to and receives power from a power supply 158 (illustratively, a battery). The controller 156 sends a retraction signal to the valve 148 to actuate the valve 148. The retraction signal may include, for example, an electrical current sufficient to heat, via a valve actuator 152 provided as a heating element, and thereby melt a valve element 150 provided as a meltable element. The controller 156 may send the retraction signal to the valve 148 in response to receiving a sensor signal from a sensor 160 operatively coupled to the controller 156. The sensor 160 may send the sensor signal in response to sensing various types of inputs. For example, the sensor 160 may be configured to determine the position of the syringe piston 128 in the syringe chamber 124 (for example, to determine if the syringe piston 128 has been moved toward the syringe outlet portion 130, thereby indicating that the therapeutic agent has been discharged from the needle 18). More specifically, the sensor 160 may be a hall effect sensor that is configured to sense the magnetic component 132 carried by the syringe piston 128. As another example, the sensor 160 and/or target 132 may be an optical sensor or a vibration sensor. As yet another example, the sensor 160 may be configured to sense when the user input 24 is actuated, and the controller 156 may then send the retraction signal after a predetermined time period. In these embodiments, the sensor 160 may be, for example, an electrical switch.

FIG. 19 illustrates an inflatable device 146 that may provide the second chamber 142 of the retraction mechanism 134 (both shown elsewhere). The inflatable device 146 is shown as an inflatable bellows having a generally semi-annular shape. The inflatable device 146 may alternatively take various other forms. For example, the inflatable device 146 may be an inflatable bellows having a different shape. As another example, the inflatable device 146 may be an inflatable bladder, an inflatable balloon, or the like. The inflatable device 146 has an inflation port 147 in fluid communication with passageway 136 (shown elsewhere). The inflatable device 146 is carried within the housing 12 between the inwardly extending flange 38 of the proximal housing portion 26 and the retraction ring 133 of the syringe assembly 116 (both shown elsewhere). Accordingly and as described in further detail below, inflation of the inflatable device 146 facilitates relative motion between the syringe assembly 116 and the housing 12, which facilitates moving the needle 18 (shown elsewhere) from the deployed configuration to the retracted configuration.

Figure 20:
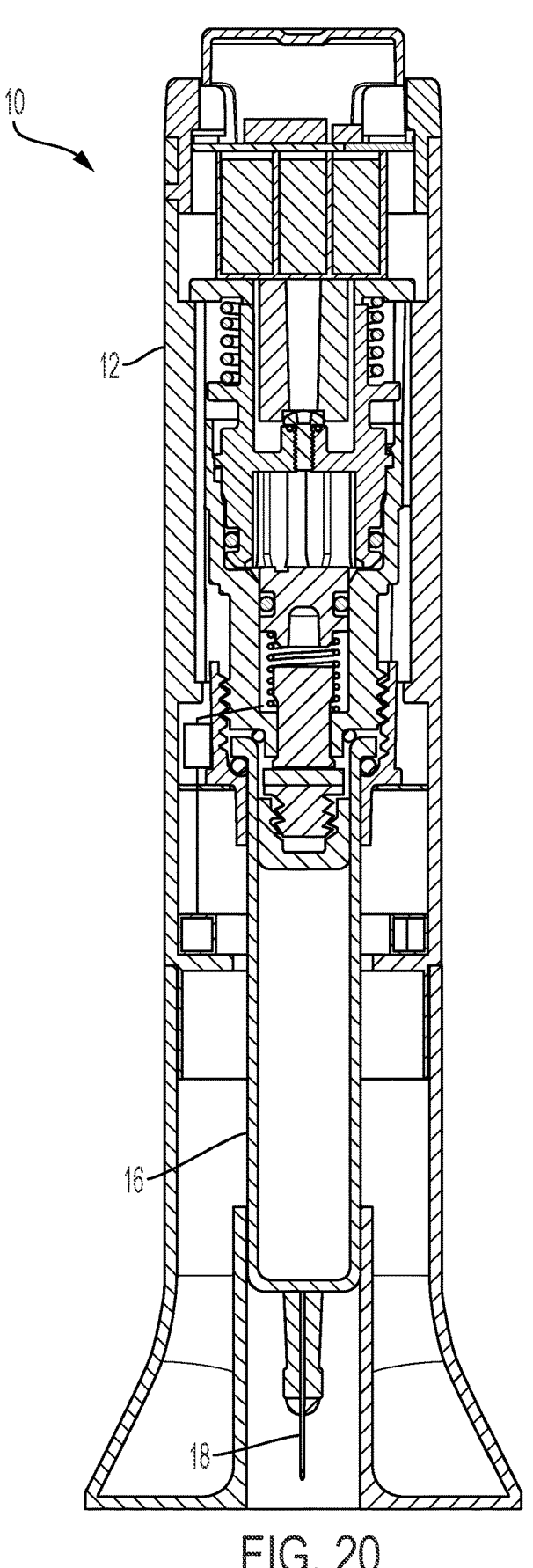
FIG. 20 is a longitudinal sectional view of the therapeutic agent delivery system of FIG. 1 in an initial or first configuration.

Illustratively, actuation of the therapeutic agent delivery system 10 is as follows. Referring to FIG. 20, the therapeutic agent delivery system 10 is illustrated in an initial or first configuration. In the first configuration, the therapeutic agent delivery assembly 16 is disposed in the stowed configuration (illustratively, a configuration in which the needle 18 is disposed entirely within the housing 12).

Figure 21:
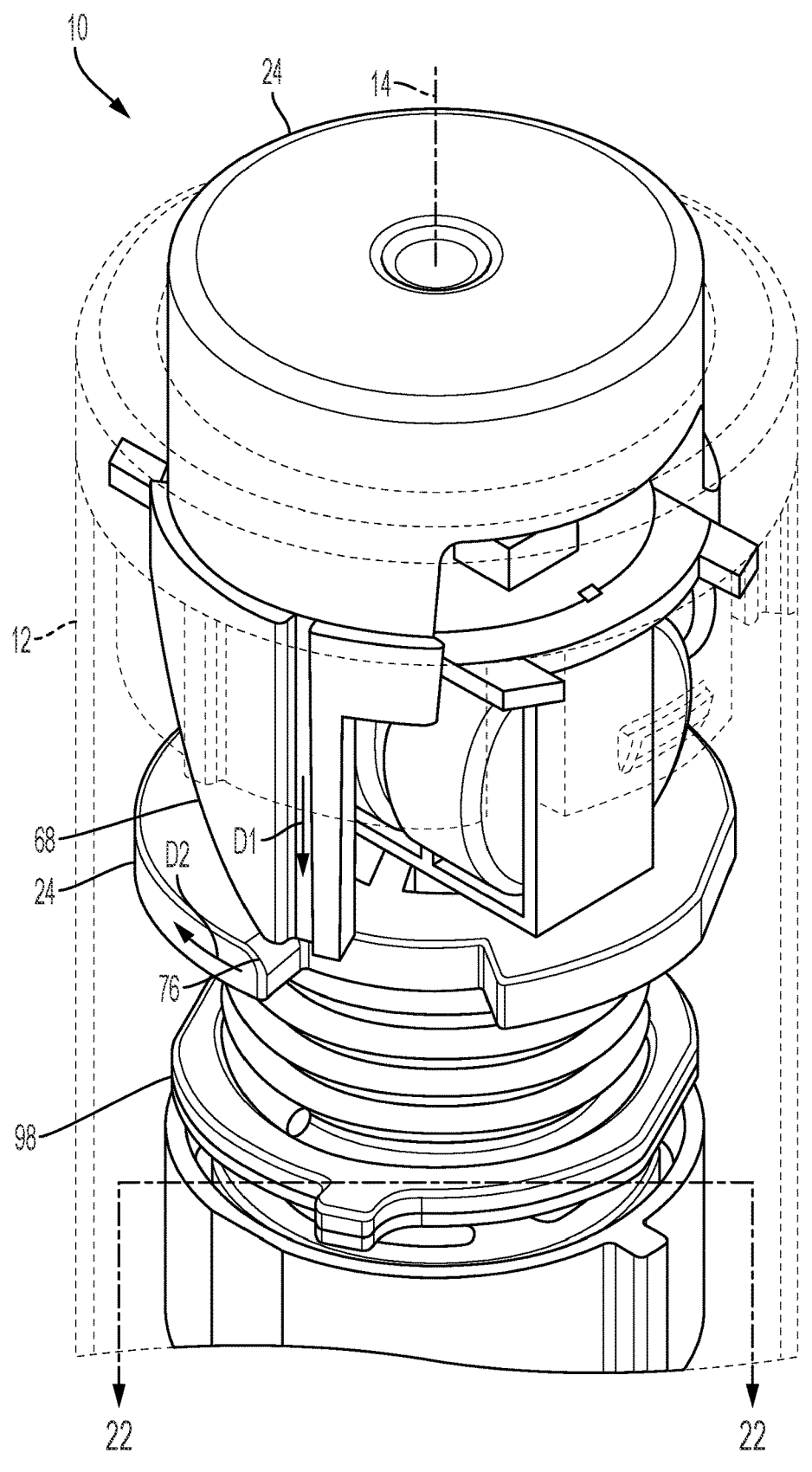
FIG. 21 is a detail top perspective view of a proximal end portion of the therapeutic agent delivery system of FIG. 1 in the first configuration; several external components are shown in hidden lines to illustrate internal components.
Figure 22:
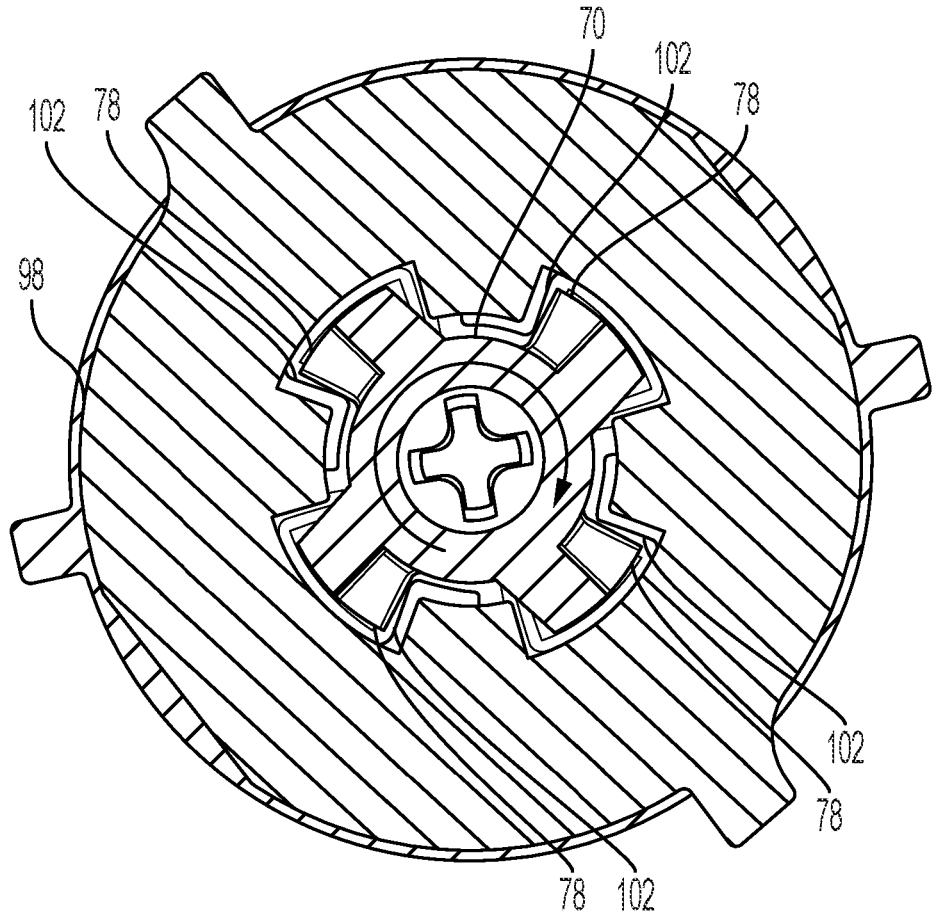
FIG. 22 is a cross sectional view of the therapeutic agent delivery system through an input drive and a shuttle of a pressure generating actuator upon actuating a user input.

Referring to FIG. 21, the user input 24 and the input drive 70 are illustrated in the first configuration. In this configuration, the user input 24 may be actuated by a user to actuate the therapeutic agent delivery system 10. More specifically, the user input 24 may be pressed and translated in a direction D1 (which may be, for example, substantially parallel to the longitudinal axis 14 (that is, parallel ±5 degrees)) relative to the housing 12. This action causes the actuation surfaces 68 of the user input 24 to engage the actuation surfaces 76 of the input drive 70. The user input 24 thereby rotates the input drive 70 in a direction D2. This action in turn causes, as shown in FIG. 22, the ledges 78 of the input drive 70 to slide over and disengage the ledges 102 of the shuttle 98.

Figure 23:
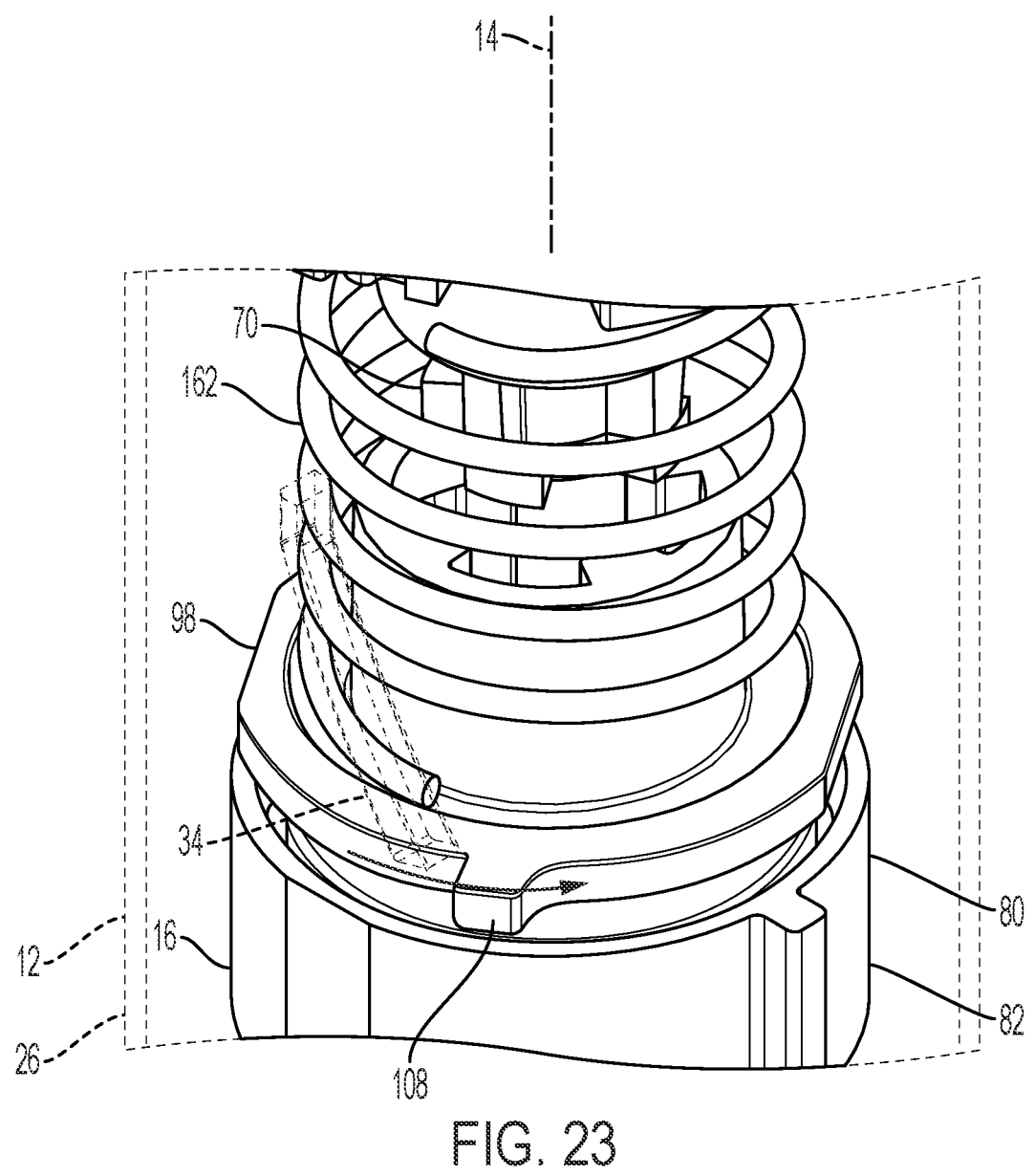
FIG. 23 is a detail top perspective view of the therapeutic agent delivery system of FIG. 1 upon a deployment spring expanding and moving the therapeutic agent delivery assembly distally relative to the housing; several external components are shown in hidden lines to illustrate internal components.
Figure 24:
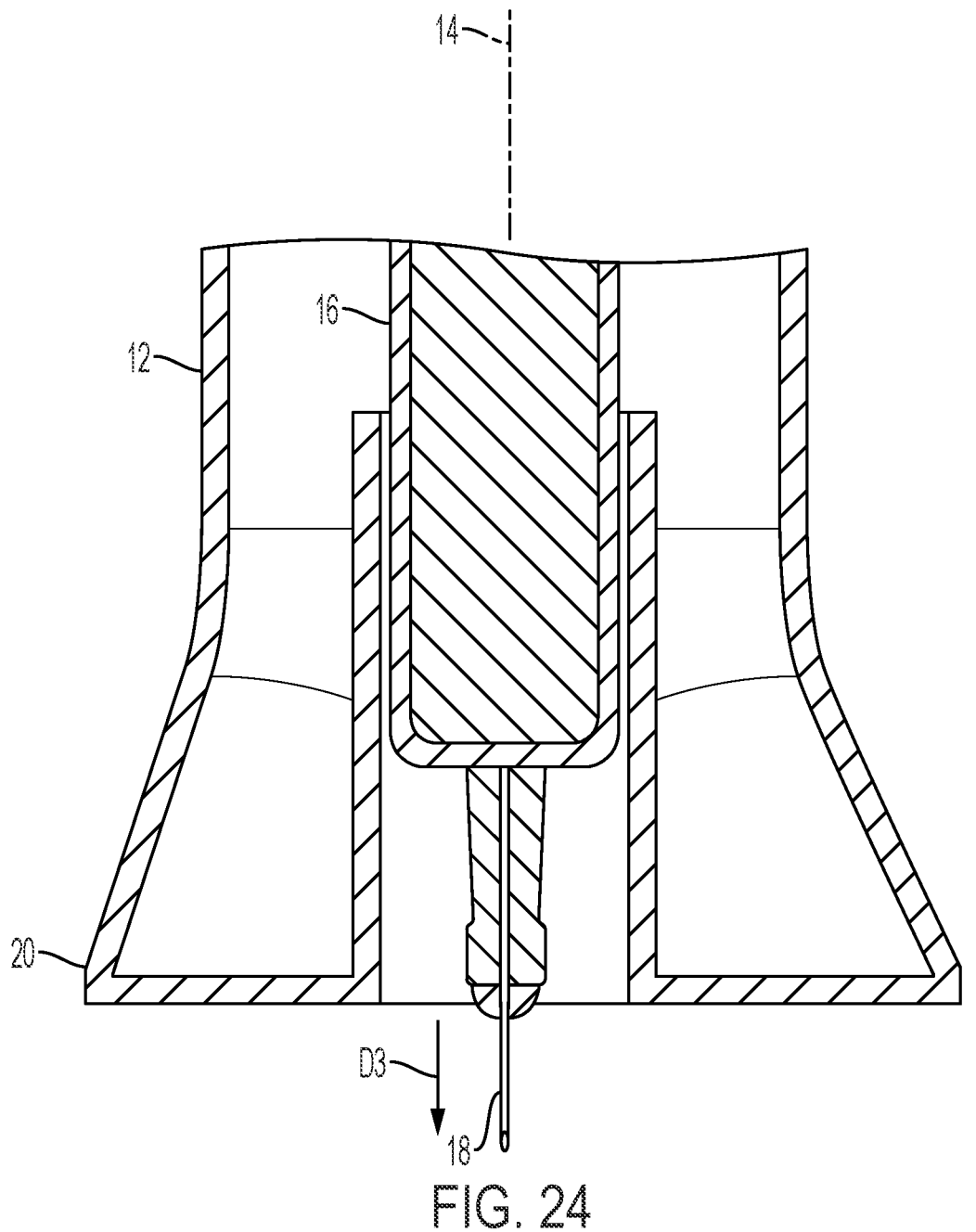
FIG. 24 is a longitudinal sectional partial view of the therapeutic agent delivery system of FIG. 1 upon the therapeutic agent delivery assembly moving to a deployed configuration.

As shown in FIG. 23, a compression spring 162 disposed between the input drive 70 and the shuttle 98 is relatively unconstrained upon disengagement of the input drive 70 and the shuttle 98. As such, the compression spring 162 expands and, as shown in FIG. 24, drives the therapeutic agent delivery assembly 16 distally relative to the housing 12. The therapeutic agent delivery assembly 16 thereby moves from the stowed configuration to the deployed configuration (illustratively, a configuration in which the needle 18 is partially exposed at the distal end portion 20 of the housing 12 and configured to engage the subject and deliver the therapeutic agent to the subject). Illustratively, the needle 18 translates from the stowed configuration to the deployed configuration in a direction D3 that is substantially parallel to the longitudinal axis 14 (that is, parallel ±5 degrees).

Figure 26:
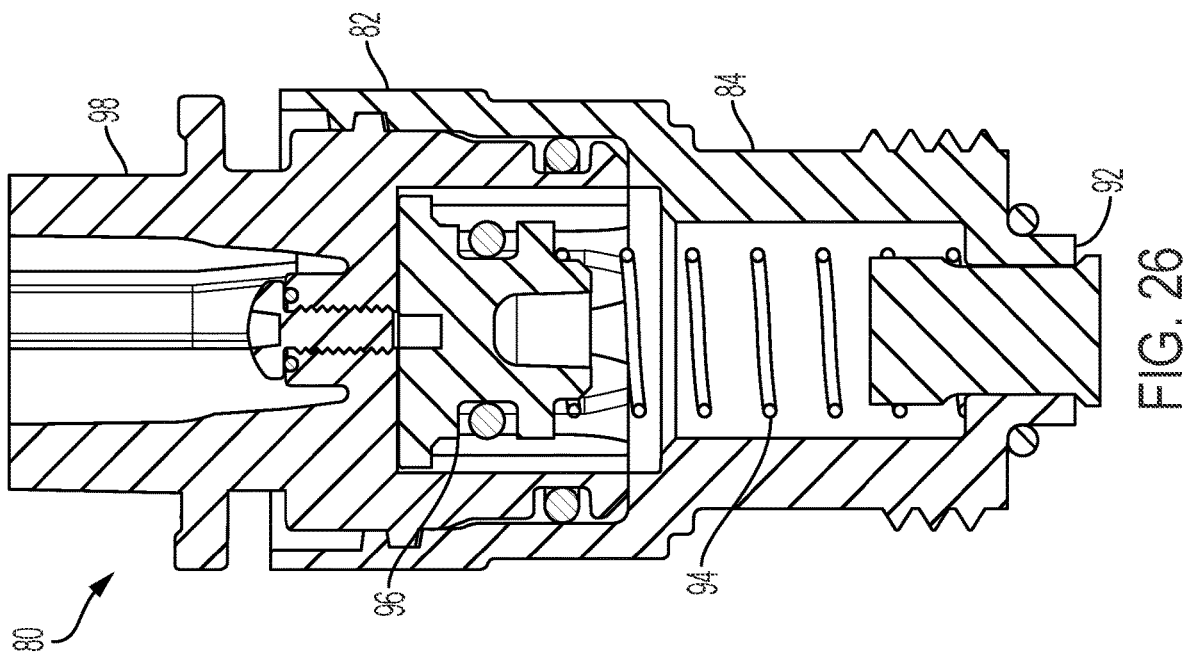
FIG. 26 is a longitudinal sectional view of the shuttle and a mixing piston of the pressure generating actuator in a deployed configuration.
Figure 25:
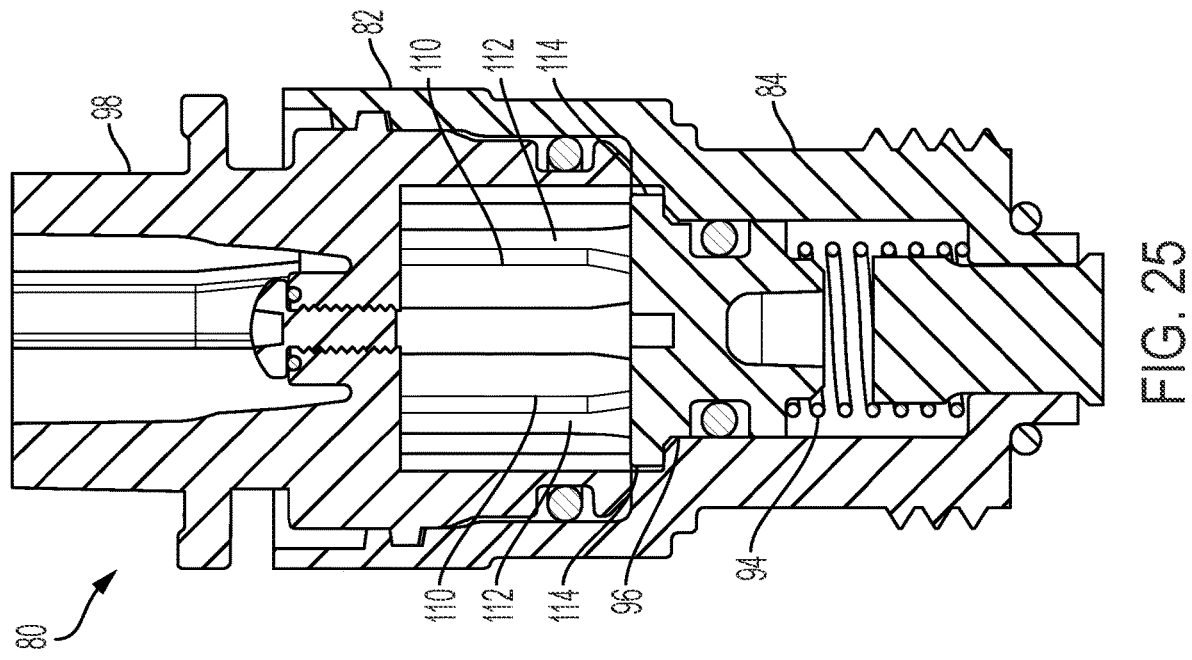
FIG. 25 is a longitudinal sectional view of a shuttle of the pressure generating actuator being rotated relative to first and second mixing chambers of the pressure generating actuator and thereby actuating the actuator.

Referring again to FIG. 23, translation of the therapeutic agent delivery assembly 16 distally relative to the housing 12 also causes the radially-outwardly extending fingers 108 of the shuttle 98 to engage and slide over the helically extending ramps 34 of the proximal housing portion 26. This engagement causes the shuttle 98 to rotate relative to the mixing chambers 82, 84 of the pressure generating actuator 80 (illustratively, about an axis that is substantially parallel to the longitudinal axis 14 (that is, parallel ±5 degrees)), which actuates the pressure generating actuator 80. More specifically and as illustrated in FIG. 25, rotating the shuttle 98 relative to the first and second mixing chambers 82, 84 angularly misaligns the radially-inwardly extending tabs 110 of the shuttle 98 with the radially-outwardly extending tabs 114 of the mixing piston 96 and angularly aligns the channels 112 of the shuttle 98 with the radially-outwardly extending tabs 114 of the mixing piston 96. As a result, the actuator spring 94 is relatively unconstrained and, as shown in FIG. 26, the actuator spring 94 expands and translates the mixing piston 96 into the shuttle 98 and the first mixing chamber 82. The reagents in the first mixing chamber 82 and the second mixing chamber 84 then mix and react to provide a pressurized gas, which the pressure generating actuator 80 delivers from the actuator outlet 92.

Figure 27:
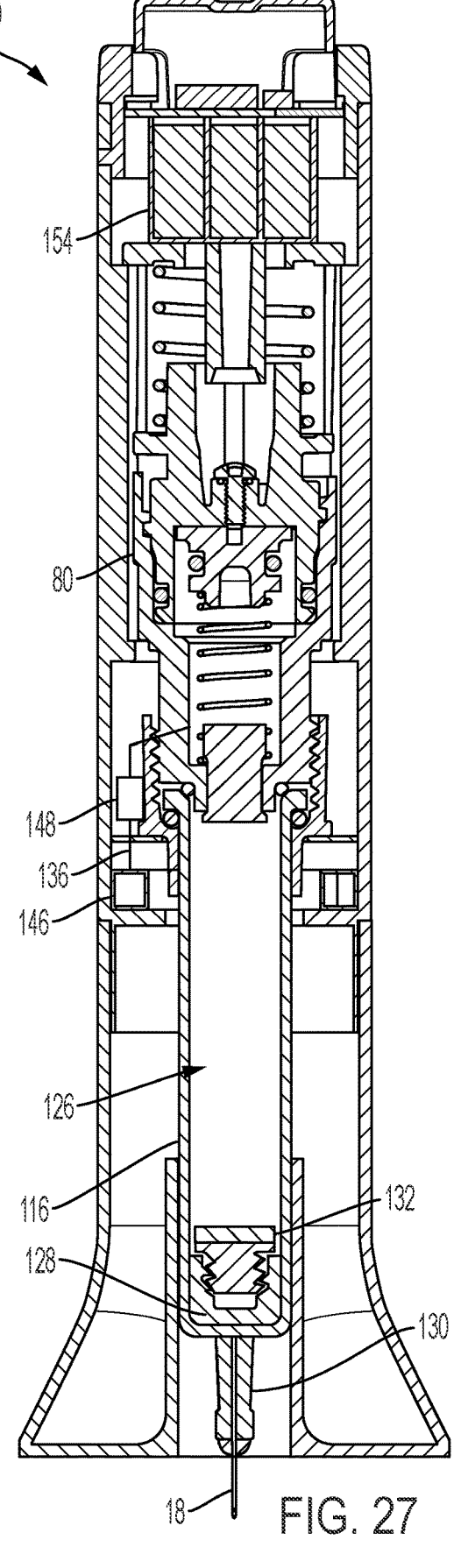
FIG. 27 is a longitudinal sectional view of the therapeutic agent delivery system of FIG. 1 upon a syringe piston moving in a syringe passageway to discharge a therapeutic agent from the needle.

Referring to FIG. 27, the pressure generating actuator 80 delivers the pressurized gas to the syringe passageway 126, which translates the syringe piston 128 distally within the syringe passageway 126. As such, the syringe piston 128 pushes the therapeutic fluid distally to the needle 18, and the needle 18 discharges the therapeutic fluid and delivers the therapeutic fluid to the subject. After delivering the therapeutic fluid to the subject (illustratively, determined by the sensor 160, shown elsewhere, sensing that the magnetic component 132, and the syringe piston 128, are disposed near the outlet portion 130 of the syringe assembly 116), the electronics assembly 154 actuates the valve 148. This action causes the pressure generating actuator 80 to deliver the pressurized fluid through the passageway 136 and to the inflatable device 146.

13

Figure 28:
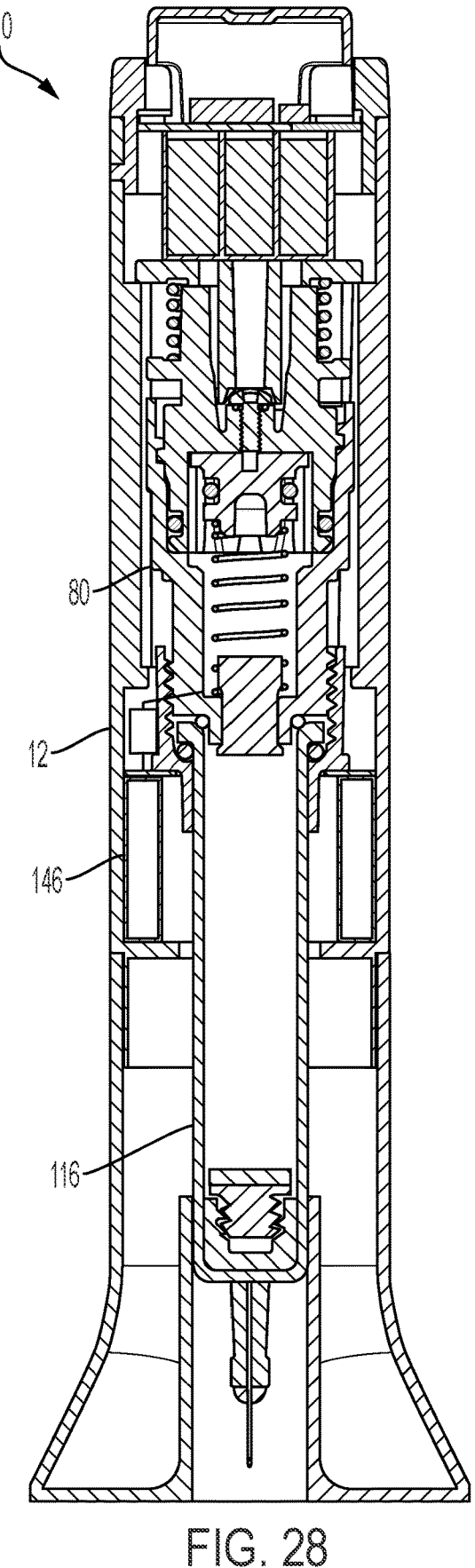
FIG. 28 is a longitudinal sectional view of the therapeutic agent delivery system of FIG. 1 with the needle in a retracted configuration.

Referring to FIG. 28, the pressurized fluid causes the inflatable device 146 to increase in volume between the inwardly extending flange 38 of the proximal housing portion 26 and the retraction ring 133 of the syringe assembly 116, which in turn proximally translates the syringe assembly 116 and the pressure generating actuator 80 relative to the housing 12. This action causes the needle 18 to translate from the deployed configuration to the retracted configuration. Illustratively, the therapeutic agent delivery system 10 cannot be actuated again (that is, the therapeutic agent delivery system 10 may be "locked out), and the therapeutic agent delivery system 10 may be discarded.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A therapeutic agent delivery system, comprising:
a housing having a distal end portion;
a therapeutic agent delivery assembly carried by the housing, the therapeutic agent delivery assembly comprising:
   a chamber comprising a first passageway configured to carry a therapeutic agent;
   a needle in communication with the first passageway;
the therapeutic agent delivery assembly being translatable relative to the housing from a stowed configuration to a deployed configuration, in the deployed configuration the needle at least partially extending distally from the distal end portion of the housing, and the therapeutic agent delivery assembly being translatable relative to the housing from the deployed configuration to a retracted configuration, in the retracted configuration the needle being disposed proximally relative to the distal end portion of the housing;
a user input configured to be actuated by a user, actuation of the user input translating the therapeutic agent delivery assembly from the stowed configuration to the deployed configuration;
a retraction mechanism being actuatable to translate the therapeutic agent delivery assembly from the deployed configuration to the retracted configuration, the retraction mechanism comprising:
   a first chamber;
   a fluid carried in the first chamber;
   an inflatable device comprising a second chamber;
   a valve being actuatable from a closed position to an open position, in the closed position the valve inhibiting fluid communication between the first chamber and the second chamber, in the open position the valve permitting fluid communication between the first chamber and the second chamber such that the first chamber delivers the fluid to the second chamber, and the inflatable device thereby inflates and translates the therapeutic agent delivery assembly from the deployed configuration to the retracted configuration.

2. The therapeutic agent delivery system of claim 1, wherein the valve comprises:
a valve element, in the closed position the valve element inhibiting fluid communication between the first chamber and the second chamber, and in the open position the valve element permitting fluid communication between the first chamber and the second chamber; and
a valve actuator coupled to the valve element, the valve actuator actuating the valve element from the closed position to the open position upon receiving a retraction signal.

3. The therapeutic agent delivery system of claim 2, wherein the valve element comprises a frangible element, and the valve actuator actuates the valve element by damaging the frangible element.

4. The therapeutic agent delivery system of claim 2, wherein the valve element comprises a meltable element, the valve actuator comprises a heating element, and the valve actuator actuates the valve element by delivering heat from the heating element to the meltable element and thereby melting the meltable element.

5. The therapeutic agent delivery system of claim 2, further comprising an electronics assembly, the electronics assembly comprising a sensor configured to sense discharge of the therapeutic agent from the needle, and the electronics assembly being configured to send the retraction signal upon the sensor sensing discharge of the therapeutic agent from the needle.

6. The therapeutic agent delivery system of claim 1, wherein the therapeutic agent delivery assembly further comprises a pressure generating actuator, the pressure generating actuator comprising the first chamber, and wherein actuation of the user input causes the pressure generating actuator to generate the fluid via chemical reaction.

7. The therapeutic agent delivery system of claim 6, wherein actuation of the user input causes the pressure generating actuator to pressurize the therapeutic agent, deliver the therapeutic agent from the passageway to the needle, and discharge the therapeutic agent from the needle.

8. The therapeutic agent delivery system of claim 1, wherein the inflatable device comprises a bellows.

9. The therapeutic agent delivery system of claim 8, wherein the bellows comprises a semi-annular shape and extends about the therapeutic agent delivery assembly.

10. The therapeutic agent delivery system of claim 1, further comprising the therapeutic agent carried in the first passageway of the chamber.

11. A therapeutic agent delivery system, comprising:
a housing having a distal end portion;
a therapeutic agent delivery assembly carried by the housing, the therapeutic agent delivery assembly comprising:
   a chamber comprising a first passageway configured to carry a therapeutic agent;
   a needle in communication with the first passageway;
the therapeutic agent delivery assembly being translatable relative to the housing from a stowed configuration to a deployed configuration, in the deployed configuration the needle at least partially extending distally from the distal end portion of the housing, and the therapeutic agent delivery assembly being translatable relative to the housing from the deployed configuration to a retracted configuration, in the retracted configuration the needle being disposed proximally relative to the distal end portion of the housing;
a user input configured to be actuated by a user, actuation of the user input translating the therapeutic agent delivery assembly from the stowed configuration to the deployed configuration;
a retraction mechanism being actuatable to translate the therapeutic agent delivery assembly from the deployed configuration to the retracted configuration, the retraction mechanism comprising:

a first chamber;

a fluid carried in the first chamber;

a second chamber;

an electronics assembly configured to send a retraction signal;

a valve operably coupled to the electronics assembly and being actuatable from a closed position to an open position upon receiving the retraction signal, in the closed position the valve inhibiting fluid communication between the first chamber and the second chamber, in the open position the valve permitting fluid communication between the first chamber and the second chamber such that the first chamber delivers the fluid to the second chamber, and the retraction mechanism thereby translates the therapeutic agent delivery assembly from the deployed configuration to the retracted configuration.

12. The therapeutic agent delivery system of claim 11, wherein the electronics assembly comprises a sensor configured to sense discharge of the therapeutic agent from the needle, and the electronics assembly being configured to send the retraction signal upon the sensor sensing discharge of the therapeutic agent from the needle.

13. The therapeutic agent delivery system of claim 11, wherein the valve comprises:

a valve element, in the closed position the valve element inhibiting fluid communication between the first chamber and the second chamber, and in the open position the valve element permitting fluid communication between the first chamber and the second chamber; and a valve actuator coupled to the valve element, the valve actuator actuating the valve element from the closed position to the open position upon receiving the retraction signal.

14. The therapeutic agent delivery system of claim 13, wherein the valve element comprises a frangible element, and the valve actuator actuates the valve element by damaging the frangible element.

15. The therapeutic agent delivery system of claim 13, wherein the valve element comprises a meltable element, the valve actuator comprises a heating element, and the valve actuator actuates the valve element by delivering heat from the heating element to the meltable element and thereby melting the meltable element.

16. The therapeutic agent delivery system of claim 11, wherein the therapeutic agent delivery assembly further comprises a pressure generating actuator, the pressure generating actuator comprising the first chamber, and wherein actuation of the user input causes the pressure generating actuator to generate the fluid via chemical reaction.

17. The therapeutic agent delivery system of claim 16, wherein actuation of the user input causes the pressure generating actuator to pressurize the therapeutic agent, deliver the therapeutic agent from the passageway to the needle, and discharge the therapeutic agent from the needle.

18. The therapeutic agent delivery system of claim 11, further comprising the therapeutic agent carried in the first passageway of the chamber.

* * * * *